(12) United States Patent
Smith

(10) Patent No.: US 9,778,027 B1
(45) Date of Patent: Oct. 3, 2017

(54) APPARATUS AND METHOD FOR IMAGING FEET

(71) Applicant: Northwest Podiatric Laboratory, Inc., Blaine, WA (US)

(72) Inventor: Christopher E. Smith, Custer, WA (US)

(73) Assignee: Northwest Podiatric Laboratory, Inc., Blaine, WA (US)

( * ) Notice: Subject to any disclaimer, the term of this patent is extended or adjusted under 35 U.S.C. 154(b) by 0 days.

(21) Appl. No.: 14/756,576

(22) Filed: Sep. 18, 2015

Related U.S. Application Data

(63) Continuation-in-part of application No. 13/998,403, filed on Oct. 28, 2013, now Pat. No. 9,194,696, and
(Continued)

(51) Int. Cl.
| | |
|---|---|
| *G01B 11/24* | (2006.01) |
| *A43D 1/02* | (2006.01) |
| *A43B 17/00* | (2006.01) |
| *A43B 7/14* | (2006.01) |
| *A61B 5/107* | (2006.01) |
| *A61B 5/00* | (2006.01) |

(Continued)

(52) U.S. Cl.
CPC .............. *G01B 11/24* (2013.01); *A43B 7/141* (2013.01); *A43B 17/00* (2013.01); *A43D 1/025* (2013.01); *A61B 5/1077* (2013.01); *A61B 5/1079* (2013.01); *A61B 5/0082* (2013.01); *A61B 5/103* (2013.01); *A61B 5/107* (2013.01); *A61B 5/6829* (2013.01); *A61D 1/02* (2013.01)

(58) Field of Classification Search
CPC ......... G01B 11/24; A43B 7/141; A43B 17/00; A43D 1/025; A43D 1/02; A61B 5/1077; A61B 5/1079; A61B 5/0082; A61B 5/6829; A61B 5/103
USPC ..... 33/3 A, 515, 227, 228; 36/112; 382/100, 382/190, 195, 199, 203, 307, 317; 600/415, 592; 378/208, 209; 348/77, 348/135

See application file for complete search history.

(56) References Cited

U.S. PATENT DOCUMENTS

| | | |
|---|---|---|
| 2,082,912 A | 6/1937 | Russell |
| 2,657,463 A | 11/1953 | Spencer |

(Continued)

*Primary Examiner* — R. A. Smith
*Assistant Examiner* — Tania Courson
(74) *Attorney, Agent, or Firm* — Todd N. Hathaway

(57) ABSTRACT

An apparatus and method for determining contours of a patient's foot ankle and lower leg. The apparatus includes an alignment structure that orientates the foot for imaging. The alignment structure includes at least one support member that engages the plantar surface of the foot substantially only in the immediate area of the lateral metatarsal heads of the foot, preferably the fifth metatarsal head. The support generates a dorsally-directed force that locks the midtarsal joint. The alignment structure further includes a saddle that engages the rearfoot and a laser beam for aligning the second metatarsal head with the distal one-third of the lower leg to place the subtalar joint in a neutral condition. The foot is thus suspended in space such that imaging is able to produce an accurate measurement of the subject areas of the foot, ankle and lower leg without distortion of the soft tissues or bone structure.

33 Claims, 26 Drawing Sheets

Related U.S. Application Data a continuation of application No. 12/924,669, filed on Sep. 30, 2010, now Pat. No. 8,567,081.

(60) Provisional application No. 62/123,600, filed on Nov. 21, 2014.

(51) Int. Cl.
*A61D 1/02* (2006.01)
*A61B 5/103* (2006.01)

(56) References Cited

U.S. PATENT DOCUMENTS

| | | | |
|---|---|---|---|
| 2,795,953 A | 6/1957 | Makowsky | |
| 3,192,627 A | 7/1965 | Levitt et al. | |
| 3,766,384 A | 10/1973 | Anderson | |
| 4,267,728 A | 5/1981 | Manley et al. | |
| 4,604,807 A | 8/1986 | Bock et al. | |
| 4,662,079 A | 5/1987 | Graf et al. | |
| 4,745,290 A | 5/1988 | Frankel et al. | |
| 5,025,476 A | 6/1991 | Gould et al. | |
| 5,164,779 A | 11/1992 | Araya et al. | |
| 5,477,371 A * | 12/1995 | Shafir | A43D 1/025 356/608 |
| 5,541,515 A | 7/1996 | Tsujita | |
| 5,640,779 A | 6/1997 | Rolloff | |
| 5,671,055 A | 9/1997 | Whittlesey et al. | |
| 5,689,446 A | 11/1997 | Sundman et al. | |
| 5,753,931 A | 5/1998 | Borchers et al. | |
| 5,804,830 A | 9/1998 | Shafir | |
| 6,006,412 A | 12/1999 | Bergmann et al. | |
| 6,160,264 A | 12/2000 | Rebiere | |
| 6,163,971 A | 12/2000 | Humphries, Jr. et al. | |
| 6,205,230 B1 | 3/2001 | Sundman et al. | |
| 6,331,893 B1 * | 12/2001 | Brown | A43D 1/02 33/3 R |
| 6,430,831 B1 | 8/2002 | Sundman | |
| 6,546,356 B1 * | 4/2003 | Genest | A43D 1/02 702/153 |
| 6,550,149 B2 | 4/2003 | Dowdell | |
| 6,654,705 B1 * | 11/2003 | Benson | A43D 1/025 702/152 |
| 6,829,377 B2 * | 12/2004 | Milioto | A43D 1/025 33/3 R |
| 6,834,437 B1 * | 12/2004 | Kilgore | A61B 5/1074 33/3 B |
| 6,969,193 B1 * | 11/2005 | Pigg | A61B 6/0421 128/882 |
| 7,051,452 B2 | 5/2006 | Brooks | |
| 7,926,363 B2 * | 4/2011 | Miller | A43B 7/141 73/862.041 |
| 7,952,727 B2 * | 5/2011 | Sundman | A43D 1/025 250/559.22 |
| 8,567,081 B2 * | 10/2013 | Smith | A61B 5/0082 33/3 A |
| 9,194,696 B2 * | 11/2015 | Smith | A61B 5/0082 |
| 9,615,814 B2 * | 4/2017 | Luo | A61B 8/0875 |
| 2002/0138923 A1 | 10/2002 | Shaffeeullah | |
| 2002/0157266 A1 | 10/2002 | Dowdell | |
| 2005/0061332 A1 | 3/2005 | Greenawwalt et al. | |
| 2005/0261869 A1 | 11/2005 | Leyerer et al. | |
| 2006/0076700 A1 | 4/2006 | Phillips | |
| 2006/0283243 A1 | 12/2006 | Peterson | |

* cited by examiner

FIG. 28B
FIG. 28A
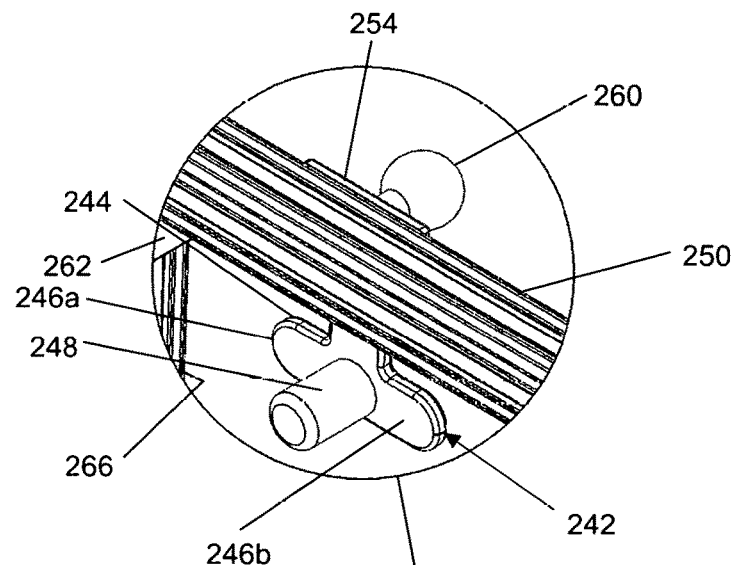
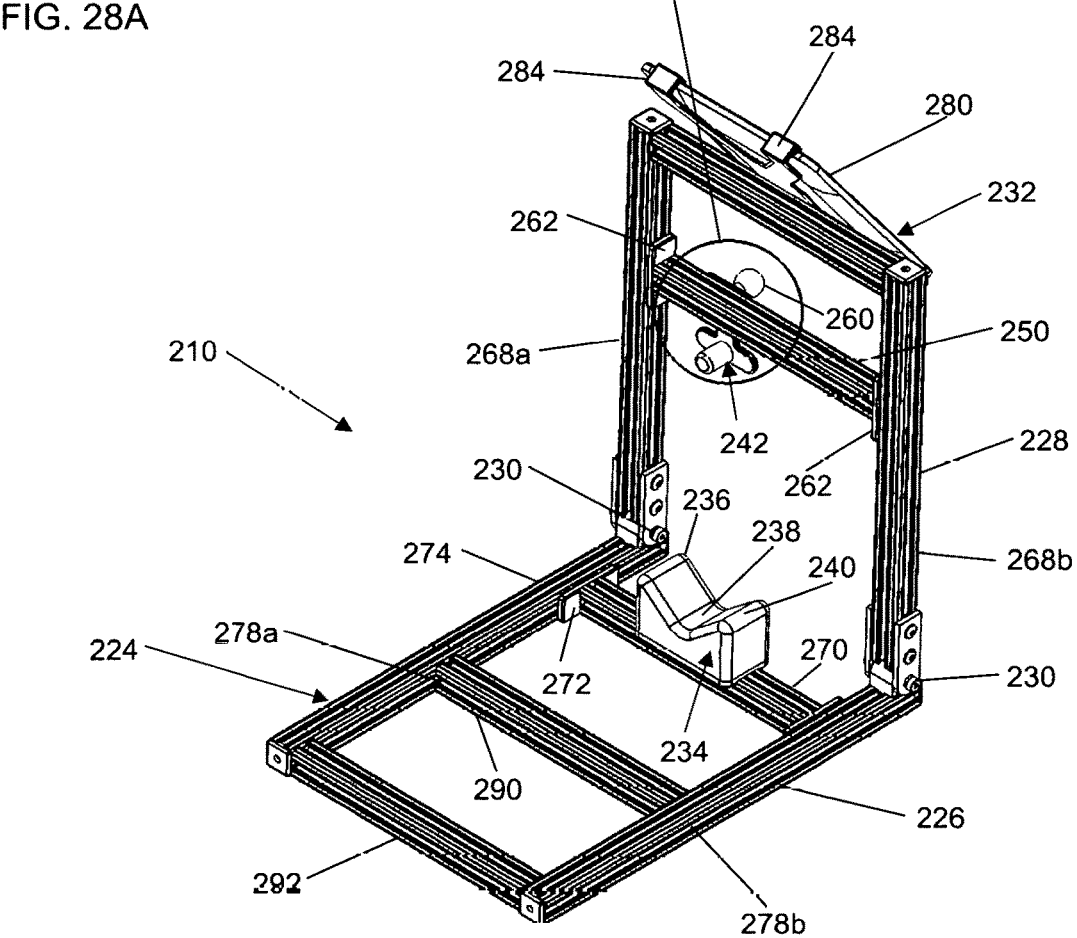

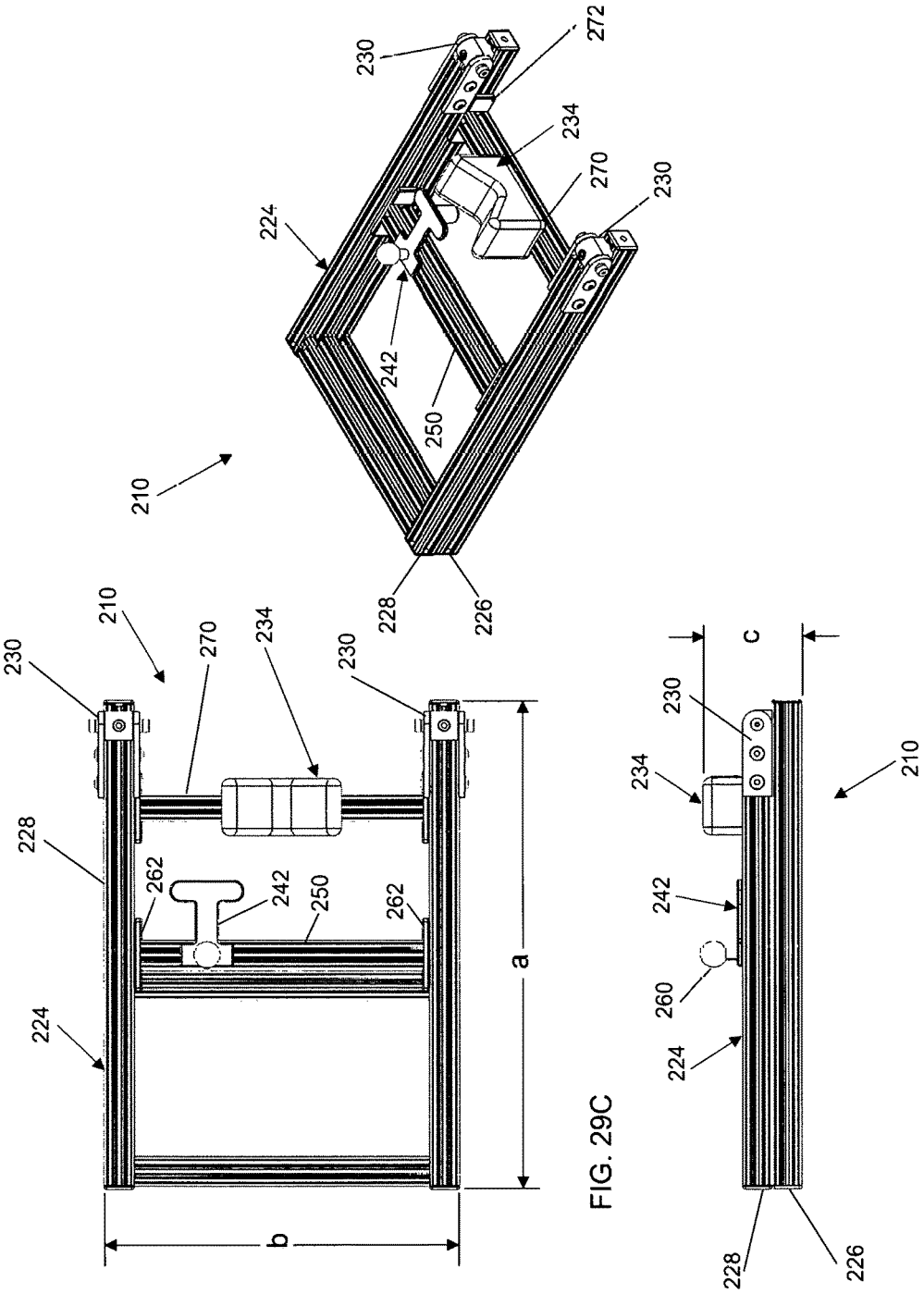

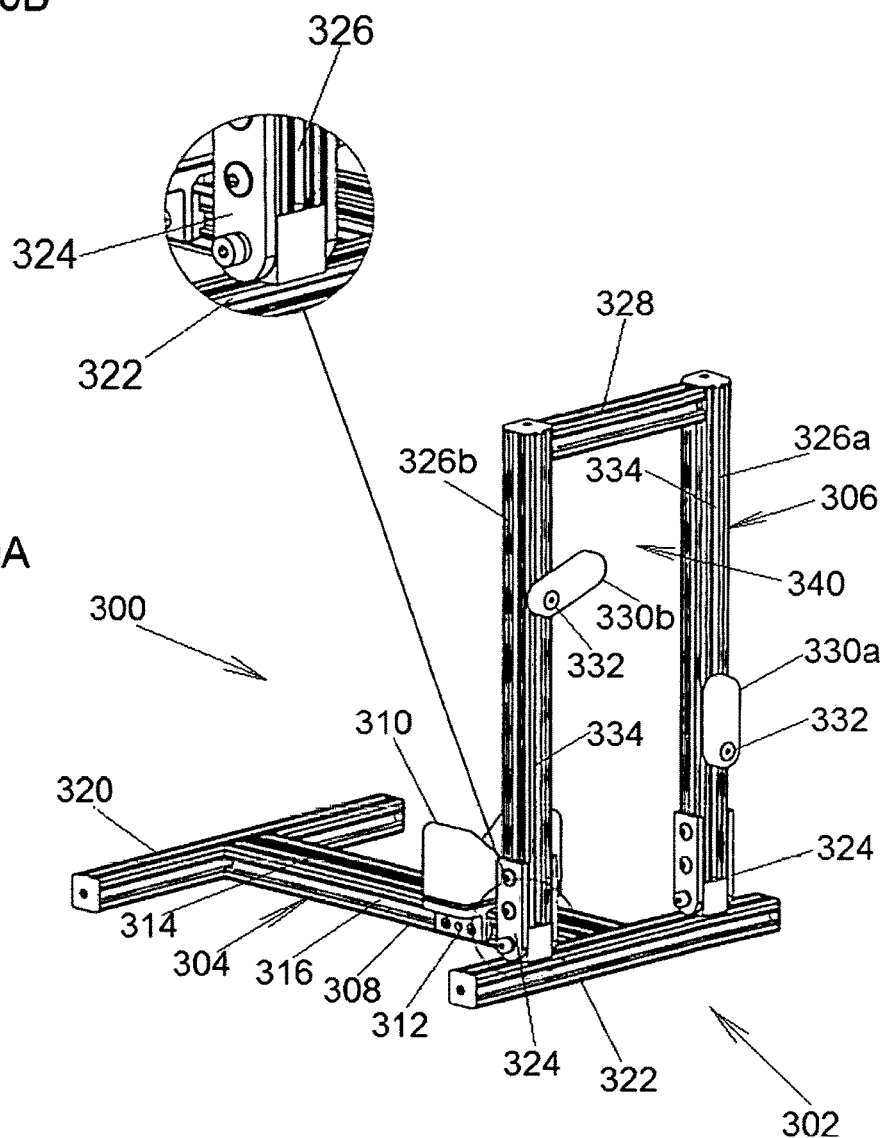

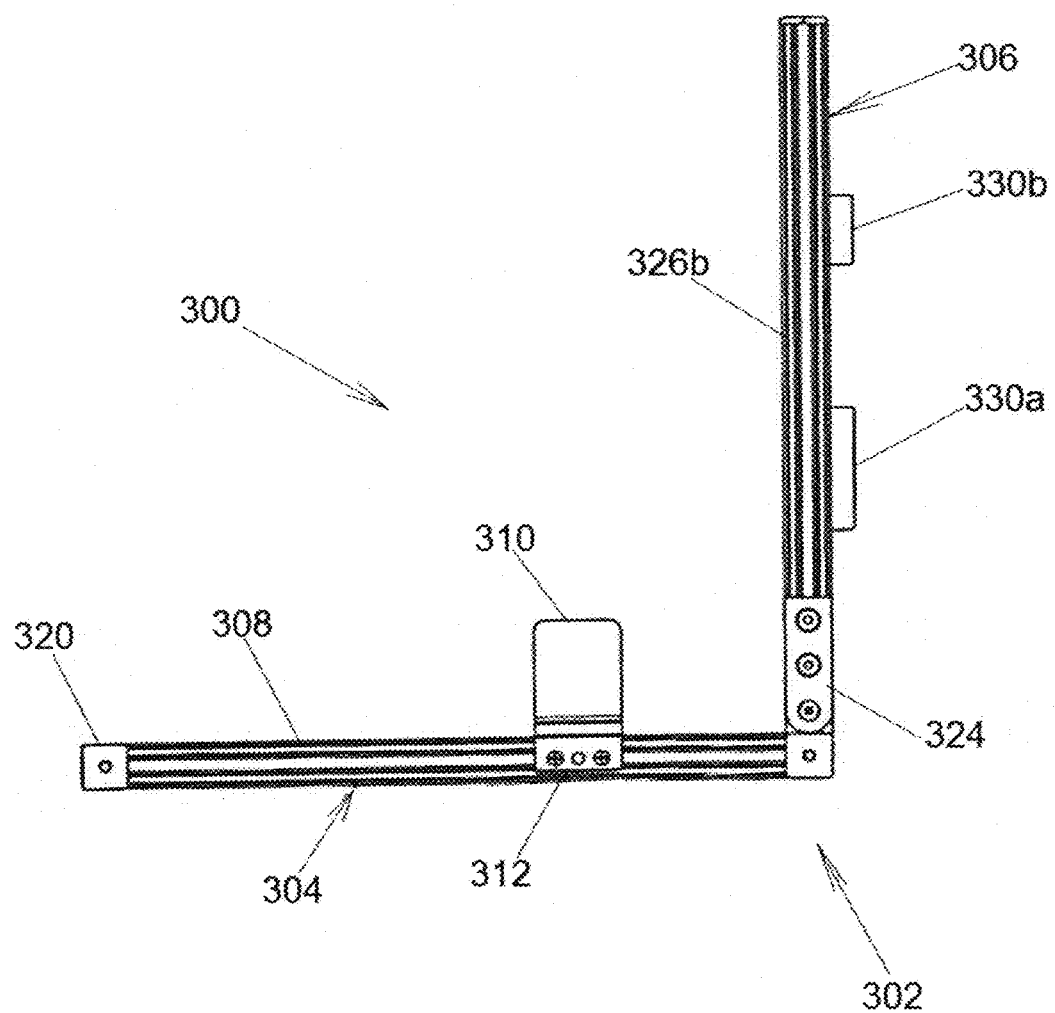

APPARATUS AND METHOD FOR IMAGING FEET

RELATED CASES

This patent application claims the benefit of U.S. Provisional Patent Application Ser. No. 62/123,600, filed Nov. 21, 2014, and is a continuation-in-part application also claiming the priority of U.S. Continuation patent application Ser. No. 13/998,403, filed Oct. 28, 2013, which claims the priority of U.S. Non-Provisional patent application Ser. No. 12/924,669, filed Sep. 30, 2010 (U.S. Pat. No. 8,567,081, issued Oct. 29, 2013), which claims the benefit of U.S. Provisional Patent Application Ser. No. 61/402,601, filed Aug. 31, 2010.

BACKGROUND a. Field of the Invention

The present invention relates generally to apparatus and methods for obtaining measurements of human feet, and, more particularly, to an apparatus and method for obtaining measurements of the contours of human feet with the feet held in a preferred physical configuration, for use in the manufacture of orthotic devices or for other purposes.

b. Related Art

Obtaining accurate measurements of the human foot, and more particularly an accurate determination of its shape and contours, is desirable for many purposes. Perhaps the most basic reason is for the sizing and fitting of shoes, but beyond this are more particular purposes such as for constructing specialized shoe inserts and other orthotic devices. In general terms, the purpose of such orthotic devices is to optimize functions of the foot and/or to correct functional problems that result from deficiencies in the bone structure and/or associated soft tissues of the foot.

Although in many cases substantial benefits can be achieved using inserts and other orthotic devices constructed on the basis of one or more standardized or idealized models of feet, the characteristics of feet naturally vary from person to person, so that in general the maximum benefits can only be provided by a custom-fitted device. This is particularly true in the case of individual feet that differ significantly from the "norm" in terms of shape, structure and/or functional abnormalities. The construction of custom orthotics and similar devices in turn depends on obtaining an accurate representation of the person's foot and of the plantar (lower) surface of the foot in particular.

One traditional technique for obtaining a representation of a patient's foot has been to obtain a direct mold of the foot. For example, the foot may be placed in or covered with a material (e.g., plaster- or resin-laden cloth) that hardens to maintain its shape, in order to obtain a negative mold of the foot. The mold is subsequently filled with plaster or other hardenable material to form a positive representation of the foot, over which the orthotic device is then molded, with corrections being made to the shape of the cast as appropriate.

Although the traditional cast-molding system described in the preceding paragraph can yield excellent results, it is by nature highly labor intensive and time-consuming in practice; furthermore, the process of applying the material to the patient's foot and allowing it to take a set while holding the foot in position requires a minimum of several minutes to complete, during which the foot must be kept essentially immobile, causing inconvenience and potential discomfort to the patient as well as being fatiguing for the clinician. Moreover, common practice is for the molds of the patient's feet to be obtained by podiatrists and other practitioners in various locales and then sent to a specialist laboratory for actual manufacture of the orthotic devices, resulting in significant delays as well as shipping costs.

An alternative to forming a mold directly from the foot is to reduce the shape/contour of the foot to some form of data that can be transmitted to the laboratory for construction of the orthotic device. In some instances, this has been done by using one or more probes or other members that physically contact the foot at a series of locations to determine its contours; for example, certain devices have utilized an array of pin-like probes that are displaced when pressed against the plantar surface of the foot (or vice versa), with various distances by which individual pins/members are displaced representing the contours of the foot.

Other approaches have utilized optics in one manner or another; for example, some systems employ laser scanning mechanisms, with the location of points along the plantar surface of the foot being calculated from an angular relationship between the laser and or other sensor, while other systems project a pattern of lines or other geometric images onto the plantar surface from which the contours can be calculated; with currently available technology, a complete laser scan of the foot requires only about fifteen seconds to complete, while digital imaging of the foot using projected lines requires a mere fraction of a second. The resulting data, typically digital, can then be conveniently transmitted to the laboratory for manufacture of orthotic devices, for example using a computer-controlled milling machine to form positive casts for molding of the orthotics, or even to form the orthotics themselves.

Systems that are able to produce digitized data accurately representing the contours of the foot, such as those noted above, offer significant advantages in terms of speed, efficiency, economy and patient comfort. However, despite these advantages such systems have on whole failed to provide entirely satisfactory results in terms of the end product, especially by comparison to the traditional molding process. One of the principal reasons, the inventor has found, is that in general such systems have necessarily imparted a degree of distortion to the foot during operation: For example, many prior optical scanners and imagers involve the patients standing on or otherwise placing their feet against a panel of glass or other transparent material, via which the plantar surfaces are exposed to the light source/sensor; pressing the foot against the panel causes the soft tissues of the foot to flatten and spread out in the areas of contact, so that when imaged the surface may be in a configuration that is far from optimal in terms of the function and comfort of the foot.

In addition to distortion of the soft tissues, a serious but somewhat more subtle problem relates to positioning of the bone structure of the foot. As is known to those skilled in the relevant art, the bone structure of the human foot transitions through a series of phases between heel strike and toe off, over what is referred to as the "gait cycle." In particular the foot transitions from an adaptive phase at heel strike, in which the bone structure is comparatively yielding and is able to collapse somewhat to absorb impact and conform to the underlying surface, to a "rigid lever" phase, as weight begins to be transferred onto the forefoot, in which the bone structure becomes more-or-less locked so that the foot can provide stability and effective propulsion at toe off. The correct "locking" of the bone structure, and more particularly of the midtarsal joint, is critical for the foot to function properly, and is therefore a central goal of functional orthotic devices. Accurately configuring an orthotic device to meet this goal, however, requires being able to ascertain the contours of the foot with the bone structure in the correct end-point condition, specifically with the subtalar joint of the foot in what is referred to as the "neutral position" and with the midtarsal joint locked, which is generally difficult or even impossible to accomplish using prior systems such as those noted above. The matter is greatly complicated by the fact that individual feet vary greatly in terms of overall orientation (e.g., in the amount of pronation) when the joints of the foot are in the correct condition.

Accordingly, there exists a need for an apparatus and method for obtaining data representing contours of a foot, accurately and without distortion of the soft tissues or bone structure of the foot. Moreover, there exists a need for such an apparatus and method that is able to obtain the data representing the contours of the foot with the structure of the foot being held in the predetermined correct condition. Still further, there exists a need for such an apparatus and method that can be employed simply, efficiently and effectively in a clinical environment, and that in use is also convenient and comfortable for the patient.

SUMMARY OF THE INVENTION

The present invention addresses the problems cited above, and provides an apparatus and method for determining contours of the surfaces of a patient's foot and associated areas of the ankle and lower leg, that holds the foot optimally positioned and configured and without distortion of the soft tissues or bone structure of the foot.

In a broad sense, the apparatus comprises (a) a support and alignment assembly that orientates the foot for imaging, the support and alignment assembly comprising at least one metatarsal head support member that engages the plantar surface of the foot substantially only beneath a lateral forefoot area of the foot; and (b) a mechanism that provides movement of the lateral forefoot area of the foot relative to the at least one metatarsal head support member so that the lateral metatarsal head area of the foot is reactively loaded in a dorsal direction by the at least one adjustable support member so as to lock the midtarsal joint.

The apparatus may further comprise an imaging device that captures an image of at least one subject area of the foot and/or the associated ankle and lower leg so as to determine contours of the subject area with the midtarsal joint of the foot locked. The imaging device may comprise a handheld imaging device that is freely movable by an operator to capture images of subject areas over a bottom and top of the foot and associated ankle and lower leg of the patient.

The at least one metatarsal head support member may comprise at least one support member that engages the plantar surface of the foot substantially only beneath an area of the fourth and fifth metatarsal heads of the foot, and preferably comprises a support member that engages the plantar surface of the foot substantially only beneath the fifth metatarsal head of the foot. The alignment and support structure may further comprise a foot engagement member that supports the foot and also the distal aspect of the leg for imaging.

The support and alignment assembly may comprise a collapsible frame assembly having the at least one metatarsal head support member mounted thereon. The collapsible frame assembly may comprise an upright frame section having the at least one metatarsal head support member mounted thereon, a horizontal frame section that supports the upright frame section, and at least one hinge interconnecting the upright and horizontal frame sections so that the frame sections are selectively pivotable between an erected configuration for use and a collapsed configuration in which the frame sections fold together for transportation or storage. The collapsible frame may have end and side areas that are open to expose plantar and side surfaces of the foot for imaging by a portable imaging device. The portable imaging device may be, for example, a portable tablet computer or camera equipped to capture digital images of the surfaces of the foot.

The at least one metatarsal head support member may comprise a support member that is vertically adjustable in the upright frame section so as to accommodate different lengths of feet. The at least one metatarsal head support member also may comprise a support member that is horizontally adjustable in the upright frame section so as to accommodate different widths of feet.

The at least one metatarsal head support member may comprise right and left metatarsal head support members mounted separately on opposite sides of the upright section of the frame assembly. In another aspect, the at least one metatarsal head support member may comprise first and second metatarsal head supports mounted as an opposing pair in sliding engagement with a cross member of the upright section of the frame assembly so as to be selectively movable between opposite sides thereof.

The mechanism that provides movement of the lateral forefoot area of the foot relative to the at least one support member may comprise at least one foot engagement member that is mounted to the frame for movement in a direction distal from the patient towards the at least one support member that is mounted to the frame. The rearfoot support assembly may be mounted on the horizontal section of the frame assembly, and the at least one metatarsal head support member may be mounted on the upright section of the frame assembly. The foot engagement member may comprise a cradle that engages the rearward side of the patient's foot and that is mounted to the frame assembly for selective movement in distal and dorsal directions towards and away from the at least one metatarsal head support member on the frame assembly. The movement mechanism of the rearfoot support assembly may comprise a sliding connection between the cradle member and the frame section that permits an operator to selectively slide the cradle member towards and away from the metatarsal head support member. The mechanism that provides relative movement between the foot and at least one metatarsal head support member may also comprise a base on the frame assembly that enables and operator to roll or slide the assembly towards or away from the patient.

The invention further provides a method for determining contours of a patient's foot. The method may comprise the steps of providing a support and alignment assembly that orientates the foot for imaging, the support and alignment assembly comprising at least one metatarsal head support member that engages a plantar surface of the foot substantially only beneath a lateral forefoot area of the foot, providing movement of the lateral forefoot area of the foot relative to the at least one metatarsal head support so that the lateral forefoot area of the foot is reactively loaded in a dorsal direction by the at least one metatarsal head support member so as to lock a midtarsal joint of the foot, and capturing an image of at least one subject area of the foot so as to determine contours of the subject area of the foot with the midtarsal joint of the foot locked.

In a broad aspect, the method comprises the steps of providing at least one metatarsal head support member that engages a plantar surface of the foot substantially only beneath a lateral forefoot area of the foot, moving the foot relative to the at least one metatarsal head support member so that the lateral forefoot area of the foot is reactively loaded in a dorsal direction by the at least one support member so as to lock a midtarsal joint of the foot, and capturing an image of at least one subject area of the foot and/or associated ankle and lower leg so as to determine contours of the subject area with the midtarsal joint of the foot locked. The step of capturing an image of the at least one subject area may comprise capturing an image of the at least one subject area by directing a digital imaging device over a bottom and top of the foot and over the associated ankle and lower leg of the patient.

The step of providing at least one metatarsal head support member may comprise providing at least one metatarsal head support member that engages the plantar surface of the foot substantially only beneath an area of the fourth and fifth metatarsal heads of the foot, and may comprise providing a metatarsal head support member that engages the plantar surface of the foot substantially only beneath the fifth metatarsal head.

The step of providing the at least one metatarsal head support member may comprise providing a support and alignment assembly that orientates the foot for imaging and that has the at least one metatarsal head support member mounted thereon. The step of providing a support and alignment assembly may comprise providing a support and alignment assembly having a frame that is collapsible from an erected configuration for use to a collapsed configuration for transportation or storage.

The step of moving the lateral forefoot area of the foot relative to the at least one metatarsal head support member so that the lateral forefoot area of the foot is reactively loaded in a dorsal direction by the at least one metatarsal head support member may comprise engaging the foot with a foot engagement member of the support and alignment assembly, and translating the foot engagement member towards the at least one metatarsal head support member so that the lateral forefoot area of the foot moves into contact with the at least one metatarsal head support member and is reactively loaded in a dorsal direction thereby. In another aspect, the step of moving the foot relative to the at least one metatarsal head support member may comprise maintaining the foot in alignment with the support and alignment assembly, and translating the support and alignment assembly towards the foot so that the at least one metatarsal head support member moves into contact with the lateral forefoot area of the foot and the lateral forefoot area is relatively loaded in a dorsal direction thereby.

In another aspect, the step of moving the lateral forefoot area of the foot relative to the at least one metatarsal head support member may comprise positioning a plantar surface of a heel of the foot against a heel support member substantially in a common plane with the metatarsal head support member and plantarflexing the foot against the metatarsal head support member to reactively load the lateral forefoot area of the foot in the dorsal direction.

The method may further comprise the step of constructing an orthotic device from the contours determined from the image captured of at least one subject area of the foot and/or associated ankle and lower leg. The step of constructing an orthotic device may comprise constructing an orthotic shoe insert from contours determined from images captured of a plantar surface of the foot. The step of constructing an orthotic device may also comprise constructing an ankle foot orthotic from contours determined from images captured of an upper portion of the foot and from surfaces of the associated ankle and lower leg.

The method may further comprise the step of determining a volume of the subject area of the foot and/or associated ankle and lower leg from the contours determined from images captured of at least one subject area. The method may further comprise the step of constructing an orthotic device that cooperates with the subject area of the foot and/or associated ankle and lower leg for which the volume has been determined.

The step of constructing an orthotic device that cooperates with the subject area of the foot and/or associated ankle and lower leg may comprise comparing the determined volume of the subject area of the foot and/or associated ankle and lower leg with an interior volume of an article that receives the foot and/or associated ankle and lower leg so as to determine a remaining volume within the article, and constructing the orthotic device to have a volume that corresponds to the remaining volume within the article so that in combination with the orthotic device a subject area of the foot and/or associated ankle and lower leg is received in the article with a desired degree of fit. In another aspect, the step of constructing an orthotic device that cooperates with the subject area of the foot and/or associated ankle and lower leg comprises constructing an orthotic device that surrounds the subject area of the foot and/or associated ankle and lower leg to have a volume that corresponds to the determined volume of the subject area. The step of constructing the orthotic device that surrounds the subject area of the foot and/or associated ankle and lower leg may comprise constructing an ankle-foot orthotic that engages an upper portion of the foot and surrounds sides of the associated ankle.

These and other features and advantages of the present invention will be more fully understood and appreciated from a reading of the following detailed description with reference to the accompanying drawings.

BRIEF DESCRIPTION OF THE DRAWINGS

FIG. 28A is a rear/patient end perspective view of the imaging assembly of FIG. 26, again showing the structure and components of the apparatus in greater detail;

FIG. 28B is a partial enlarged, perspective view of the adjustable metatarsal head support assembly of the apparatus of FIG. 28A and the stop member thereon that reacts against the side of the patient's foot to correctly position the support beneath the fifth metatarsal head of the foot;

FIGS. 29A, 29B and 29C are, respectively, perspective, plan and elevational views of the imaging assembly of FIG. 36, showing the assembly collapsed to a compact folding configuration for transportation or storage;

FIG. 30A is a perspective view of a portable foot imaging assembly in accordance with another embodiment of the present invention, in which adjustable right and left metatarsal head support members are mounted in first and second uprights of the frame of the assembly;

FIG. 30B is a partial, enlarged perspective view of the folding hinge mechanism of the apparatus of FIG. 30A;

FIG. 31 is a side elevational view of the imaging assembly of FIG. 30A, showing the relationship of the rear foot/lower leg cradle to the metatarsal head support members on the upright section of the frame of the assembly in greater detail;

DETAILED DESCRIPTION

Figure 1:
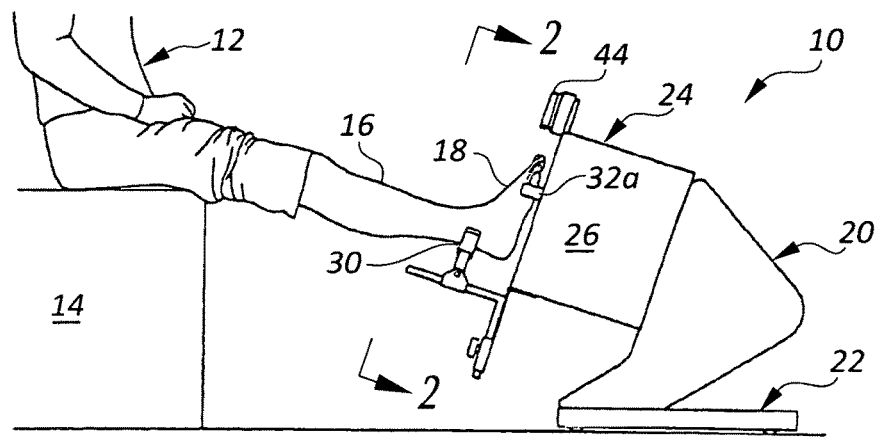
FIG. 1 is a side elevational, environmental view of a foot imaging apparatus in accordance with a preferred embodiment of the present invention, showing the apparatus with the right foot of a patient in position for imaging and measurement of the contours of the plantar surface.

FIG. 1 shows a foot imaging apparatus 10 in accordance with a first preferred embodiment of the present invention. The apparatus is shown in use in conjunction with a patient 12 in a seated position on a chair 14 or other support, with a leg 16 and foot 18 outstretched.

Figure 6:
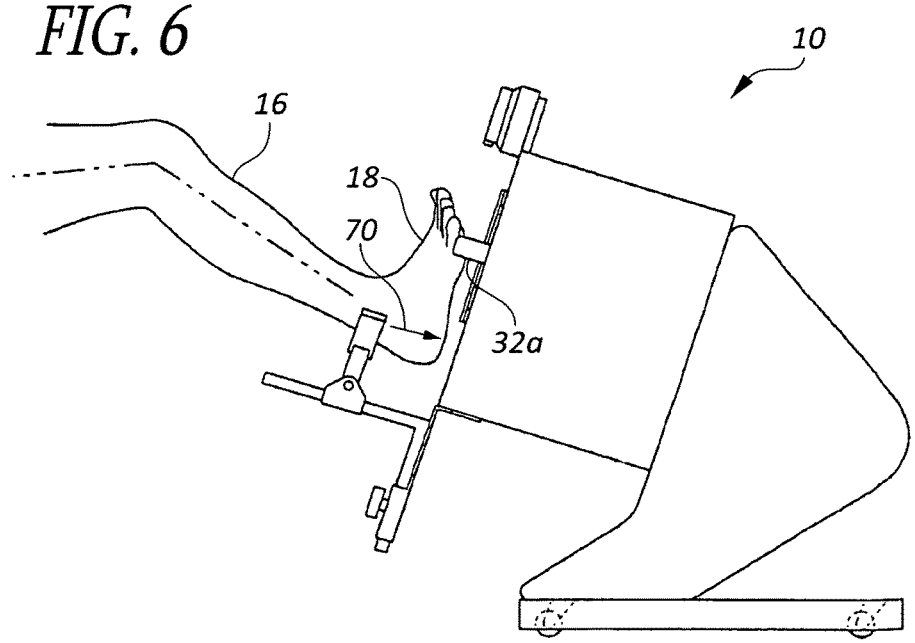
FIGS. 6-8 are sequential side elevational, environmental views of the foot imaging apparatus of FIGS. 1-3, showing the manner in which a patient's foot is placed in the heel support portion of the apparatus with the knee first raised and the ankle dorsiflexed, and the leg then straightened and the ankle plantarflexed.
Figure 7:
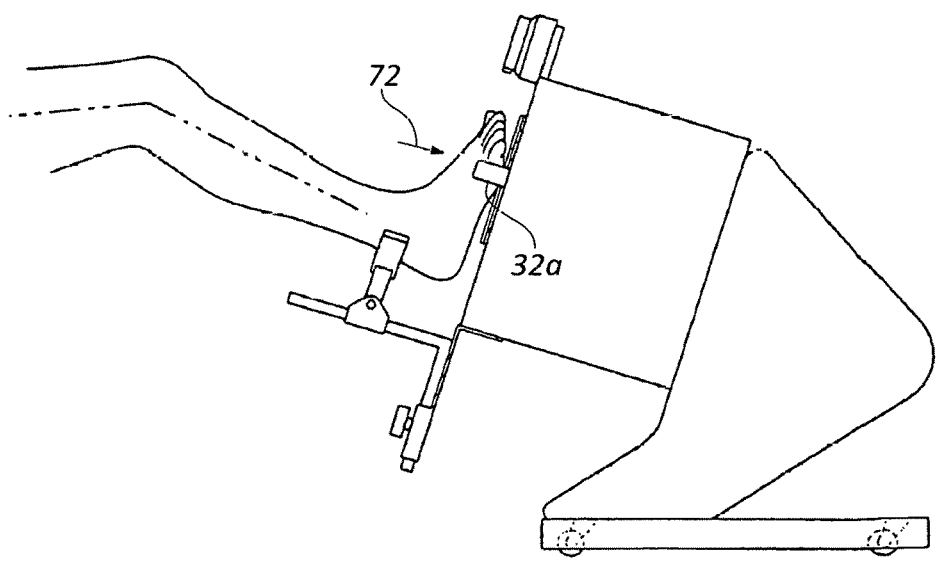
Figure 8:
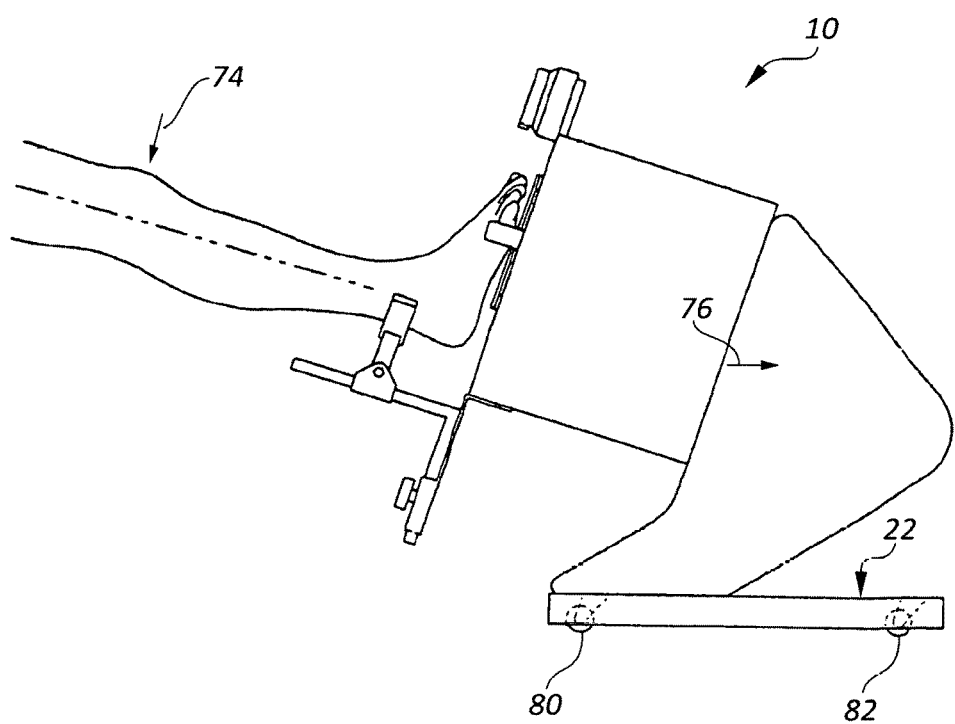

As can be seen with further reference to FIG. 1, the imaging apparatus 10 includes an optical imaging section 20 mounted on a rolling chassis section 22, and an alignment section 24 that is spaced from the imaging section 20 towards the patient's foot 18. The alignment section 24 in the illustrated embodiment includes a spacer frame 26, which in the embodiment illustrated in FIG. 6-7 is formed by a somewhat box-shaped structure, with a through passage and open ends that define an aperture 28 via which the plantar surface of the foot is exposed to the optics of the imaging section 20. A principal function of the spacer frame is to support the alignment components, as described below, such that the plantar surface of the patient's foot will be held proximate a predetermined focal length of the camera in the imaging section 20; it will therefore be understood that the shape and construction of the spacer frame are somewhat arbitrary and may vary significantly depending on design factors.

Figure 2:
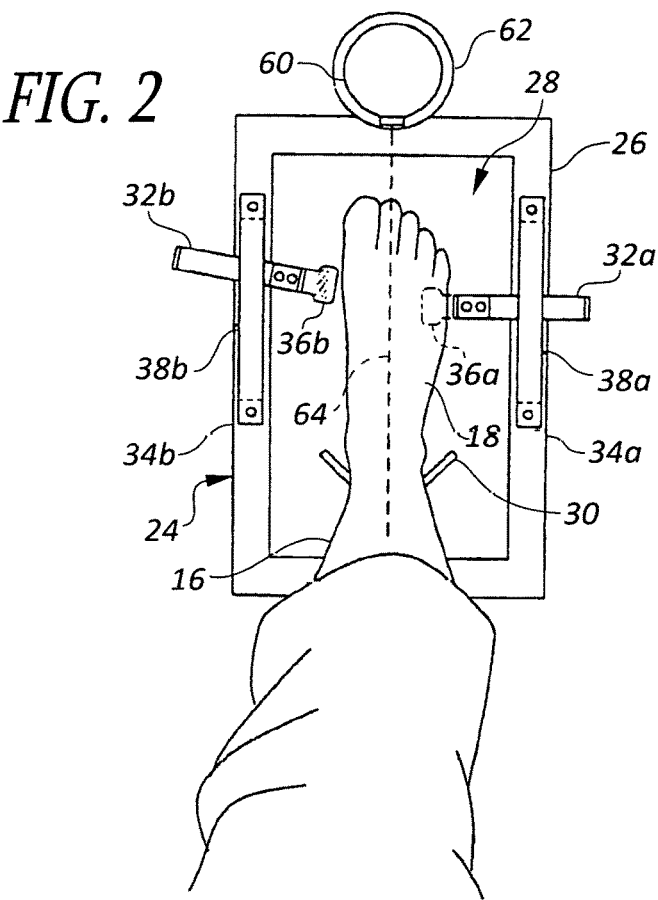
FIG. 2 is a front elevational, environmental view of the foot imaging apparatus of FIG. 1, showing the manner in which the foot is aligned with a laser pointer and also reactively loaded by a support under the fifth metatarsal head so that the foot is held in the correct condition and orientation for imaging.

As can be seen referring again to FIG. 1 and also FIG. 2, the alignment section 24 includes a set of cooperating foot alignment components that are mounted to the outer end of the spacer frame (i.e., the end facing towards the patient), namely, a heel saddle or cradle 30, right and left adjustable supports 32a, 32b for engaging the plantar surface of the foot, and a laser pointer 44 for projecting a visual reference line onto the foot. As will be described in greater detail below, the alignment components serve to position and load the foot such that the bone structure is held steady with the subtalar joint in the "neutral" position and with the midtarsal joint locked, which as explained above is critical for properly determining contours of the foot needed to construct an effective orthotic device.

As noted above, the bone structure of a functional human foot transitions through a series of phases beginning with heel strike (when the heel makes initial contact with the ground or other surface), with the bone structure initially being somewhat loose and free to collapse and spread to a degree in order to absorb shock and conform to the underlying surface. Then as weight moves forwardly on the foot, with forward motion of the body, the bone structure transitions to a comparatively rigid configuration: In particular the center of weight, as borne by the plantar surface of the foot, initially follows a somewhat forward and lateral path, as the rearfoot simultaneously undergoes eversion, with the midtarsal joint becoming "locked" as the center of weight transfers onto the area of the fifth metatarsal head (generally in the area beneath the base of the small toe). The midtarsal joint remains locked for the remainder of the gait cycle, so that the foot forms a substantially rigid "lever" for efficiently transmitting force to the ground during toe-off. A more complete explanation of the gait cycle and the locking and unlocking of the metatarsal joint is found in U.S. Pat. No. 5,960,566, which is incorporated herein by reference.

The alignment components of the present invention exploit the characteristics of the foot as a rigid lever, as described in the preceding paragraph, to locate the foot in position for imaging of its plantar surface; moreover, in the present invention this is accomplished without distorting the soft tissue or bone structure of the foot.

As can be seen in FIGS. 1-2, the heel cradle or "saddle" 30 in the illustrated embodiment is somewhat V-shaped so as to have a centering effect on the rearfoot, and therefore also the distal portion of the leg, and is spaced somewhat away from the general plane of the plantar surface, the latter being located proximate aperture 28, so as to retainingly engage the foot in the area located near the top of the heel area/bottom of the distal one-third of the lower leg, with the size and angle of the V-shaped area being configured to hold this area of the leg firmly but without discomfort to the patient. The V-shaped saddle 30 is generally located along the centerline of the aperture 28 and therefore along the axis of the imaging section, thus allowing it to be used with either right or left feet.

Figure 3:
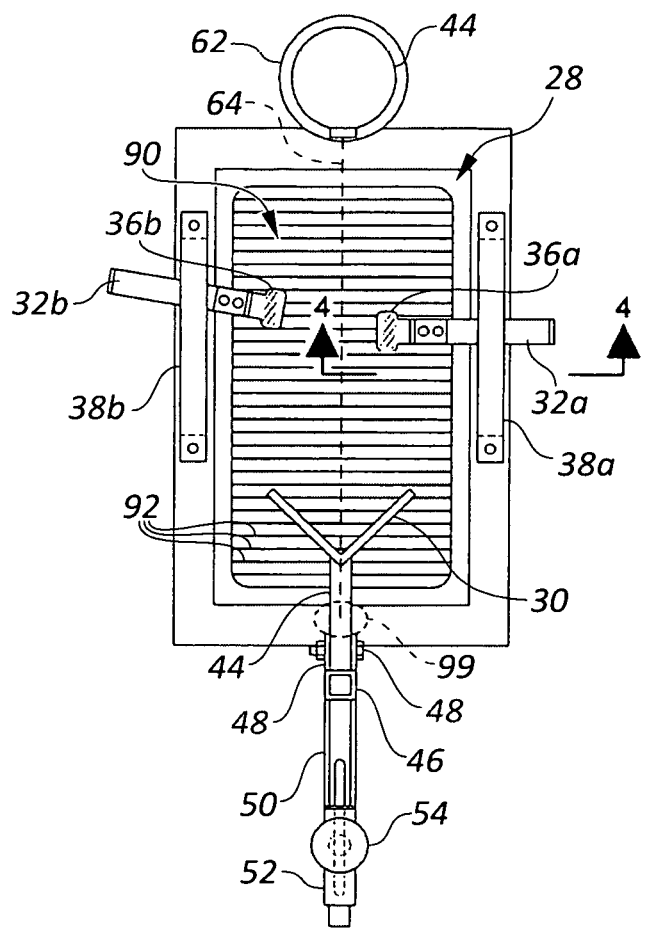
FIG. 3 is a front elevational view of the apparatus of FIGS. 1-2, with the patient's foot removed, showing the supporting structure and also the face of the optical imaging section of the apparatus.
Figure 4:
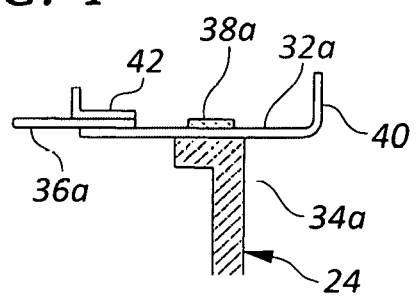
FIG. 4 is a partial cross-sectional view of the foot imaging apparatus of FIGS. 1-3, taken along line 4-4 in FIG. 3, showing the structure of the adjustable support in greater detail.

As can be seen with further reference to FIG. 2 and also FIGS. 3-4, the right and left adjustable support members 32a, 32b project inwardly towards the centerline of the aperture 28 from respective sidewalls 34a, 34b of the spacer frame 24. Pad members 36a, 36b are mounted on the inboard ends of the adjustable arms 32a, 32b, and are preferably formed of a rigid yet transparent material that is capable of applying a dorsally-directed force to the plantar surface of the foot without obscuring it from view by the imaging section, such as Plexiglas™ or Lexan™ for example. The pad members 36a, 36b are preferably sized to engage only the area of the foot immediately beneath the fifth metatarsal head, with dimensions of about 1" by 0.5" being generally suitable.

The arm members 32a, 32b are adjustable to accommodate different lengths and widths of feet; in the embodiment that is illustrated in FIGS. 1-4, the arm members 32a, 32b are held in sliding engagement against the end surfaces of the sidewalls 34a, 34b of the spacer frame 24, by guide strips 38a, 38b that are secured to the end surfaces so as to define slots sized to form a friction-fit but slidable engagement with the respective arm members. The arm members can therefore be selectively slid both longitudinally and laterally (in and out) with respect to the centerline of the aperture 28, so as to position the pads 36a, 36b beneath the fifth metatarsal head area of feet having different sizes, the right side arm and pad being used for right feet and the left side arm and pad being used for left feet. As can be best seen in FIG. 4, the arm members are preferably provided with upturned tab portions 40 on their outer ends that facilitate manual adjustment of the arm members, as well as upturned end plates 42 located at the junctions where the transparent end pads are mounted to the arm members, the latter serving to engage the sides of the foot lateral of the transparent pads so that only the transparent material extends below the plantar surface of the feet.

The position of the heel saddle 30 is also adjustable to accommodate feet and legs of different sizes. First, as can be seen in FIG. 3, the saddle is supported on the upper end of a generally vertical arm 44 that is joined to a second, generally horizontal bar by a bracket 48 that is in frictional engagement with the latter. The heel stirrup can therefore be selectively slid towards and away from the support arms 32a, 32b at aperture 28, as indicated by arrow 49 in FIG. 5, to accommodate feet having smaller/shorter or bigger/taller rearfoot areas and/or difference in the size of the distal one-third of the lower leg. The end of horizontal bar 46 is mounted to a second, generally vertical bar 50, that passes through a friction-fit sleeve 52 in sliding engagement therewith, the sleeve being fixedly mounted to the spacer frame 24 by a bracket 56; friction through the sleeve 52 is controlled by a knob 54, so that the position of the saddle is adjustable in a generally vertical direction as indicated by arrow 58 in FIG. 5.

Also mounted at the end of the spacer frame 24 proximate aperture 28 is the laser pointer 60, held in place by a support bracket 62, that projects a visible beam 64 generally along the centerline of the aperture 28 and also in alignment with the center of the V-shaped heel saddle 30 as well as the central plane of the camera 98, as indicated by the dotted-line image in FIG. 3. The laser beam thus provides a visual reference line for the center plane of the aperture 28 and the imaging area as a whole.

As was noted above, the components of the alignment section serve to orientate the bone structure of the foot with the midtarsal joint in the locked position, employing alignment of the bone structure in conjunction with a dorsally-directed (upward) loading of the fifth metatarsal head, essentially mimicking the reactive force of gravity experienced by the fifth metatarsal head at the corresponding point in the gait cycle.

The steps in accomplishing the positioning and locking of the foot are best seen in FIGS. 2 and 6-8. As an initial step, the imaging apparatus 10 is brought into proximity with the seated patient, so that the centerline that is established by the laser pointer and V-shaped heel saddle is in general alignment with and towards the user's hip on the side of the foot that is to be imaged (e.g., in general alignment with the right portion of the hip if the right foot is to be imaged). The patient's foot is then placed in the saddle 30 as shown in FIG. 6, with the knee slightly bent (raised), and with the ankle dorsiflexed and the heel thrust forward as indicated by arrow 70 in FIG. 6, so that the plantar surface of the heel is located closely proximate the plane that is defined by the adjustable pads 36a, 36b at aperture 28. In so doing, the stirrup takes the majority of the weight off of the extremity, which simultaneously centralizing the rearfoot and distal one-third of the lower leg relative to the aperture and imaging section. The clinician (operator) adjusts the respective arm member 32a, 32b so that the associated pad 36a, 36b is positioned beneath the lateral forefoot, and in particular the fifth metatarsal head of the bone structure as shown in FIG. 2, and the patient then plantarflexes the ankle joint so as to lower the forefoot as indicated by arrow 72 in FIG. 7. In so doing, the plantar surface of the forefoot in the area beneath the fifth metatarsal head comes into contact with the pad 36a/36b on the support arm, so that the fifth metatarsal head is held against further movement in the plantar direction; plantarflexing the forefoot merely requires the patient to relax the ankle from holding the foot from the "heel forward" condition in which the foot is initially set in the stirrup, so that when the forefoot is fully relaxed and lowered, the fifth metatarsal head is subject to an upward (dorsally-directed) force mimicking the loading of the fifth metatarsal head created by the force of gravity during the corresponding phase of the natural gait cycle. A dorsally-directed force sufficient to load the fifth metatarsal head to resistance is created merely by the tension exerted by the muscles of the lower leg when in a relaxed condition, acting through the Achilles tendon and with the ankle joint serving as the fulcrum, so that the midtarsal joint assumes the locked configuration without the patient having to purposely press down on the forefoot using the muscles and ligaments in a manner that might cause distortion of the foot or deviation from the correct shape, and without the area of the fifth metatarsal head having to bear excessive weight that might also cause distortion of the tissues and/or patient discomfort.

To centralize the foot relative to the central axis of the viewing area and place the subtalar joint in a neutral condition, while keeping the midtarsal joint locked, the leg is next adjusted to position the second metatarsal head (in the area proximate the base of the second toe) with the beam 64 that is projected by the laser pointer 44, the beam being aligned with the center of the heel stirrup as noted above; in the embodiment of FIGS. 1-8, centralization of the foot is achieved by sliding the adjustable arm members 32a, 32b in or out as necessary. The patient's knee is then lowered and the ankle joint concurrently plantarflexed to about 90°, as indicated by arrow 74 in FIG. 8, so as to push the apparatus 10 away from the chair or other support on which the patient is seated. In response, the apparatus rolls away from the patient over the floor on its wheeled chassis, as indicated by arrow 76 in FIG. 8; wheeled chassis 22 is supported by a pair of casters 80 at its trailing end (toward the patient) and a single caster 82 at its leading end (away from the patient), so as to permit the chassis to turn inwardly in an arc towards a patient's centerline as the apparatus moves away from the patient, thus accommodating the natural inward deviation (angle towards the midline of the body) that is present in most lower legs. The effect of the combined distal and medial motion of the apparatus is to bring the second metatarsal head of the foot into general alignment with the distal one-third of the lower leg so as to place the subtalar joint in the neutral condition, with the alignment being verified visually by the line of the laser beam pausing over the top of the second metatarsal head and up the distal portion of the lower leg. In practice, it has been found that with casters and a floor surface selected for minimal rolling resistance, the inward turning action of the cart as it rolls away from the patient very effectively obtains the correct alignment of the foot to the leg (as shown in FIG. 2) with little or no intervention or subsequent adjustment being required by the clinician; to the extent that minor corrections or "fine tuning" of the alignment is needed, this is easily performed by simply sliding the support arms in or out in the manner described above, to bring the second metatarsal head and lower third of the lower leg back into alignment with the beam of the laser.

It will be understood that other arrangements of casters or wheels may be used on the cart to allow the rolling and turning action, in addition to the "tricycle" caster arrangement described, and furthermore that in some instances the patient may be seated on a chair or other support that rolls away from and/or turns relative to the imaging apparatus rather than vice versa.

Positioned and locked in the manner described, the pad 36a/36b on which the fifth metatarsal head rests effectively establishes the transverse plane of the foot, at a position proximate the focal length of the camera of the imaging section of the apparatus. Since, in the illustrated embodiment, the V-shaped heel stirrup holds the rearfoot and distal one-third of the lower leg essentially perpendicular to the plane of the metatarsal support pads 36a, 36b, the two pads effectively establish a transverse plane of the foot at essentially 0° eversion/inversion relative to the frontal plane. However, as noted above, individual feet vary greatly, and depending on the degree of eversion exhibited by the foot (e.g., 6° everted, 8° everted, and so on), the medial aspect of the forefoot may in some instances be positioned above the 0° transverse plane or below the 0° transverse plane when the midtarsal joint is locked and the subtalar joint is in the neutral position. Therefore, another significant advantage of the present invention, in which a support exists only under the lateral forefoot and preferably only under the fifth metatarsal head rather than all the way across the foot, is that the medial aspect of the foot is free to elevate above or depress beyond the 0° transverse plane as the nature of the particular foot dictates, which is not possible in the case of devices in which the entire width of the foot is pressed against a plate of glass or other continuous support or surface.

With the foot aligned and held in the manner described, the entire plantar surface of the foot is exposed to the optical system of the imaging section of the apparatus, the area under the fifth metatarsal head being "visible" to the optics by virtue of the transparent material of which the support pads are formed. Furthermore, since the foot is centered on the central plane of the camera (at aperture 28), the camera is able to capture the image a sufficient distance up both sides (medial and lateral) of the foot, so that adequate contour data can be obtained without need for views at multiple angles or using multiple cameras. In the preferred embodiment that is illustrated in FIGS. 1-5, the imaging section utilizes a three-dimensional measurement instrument that operates on the basis of projecting a pattern of parallel lines onto the plantar surface of the foot and then capturing the resulting image using a camera set at a predetermined angle to the axis of projection, the image then being analyzed to determine the contours of the plantar surface. Such three-dimensional digitizers are available, for example, from Virtual 3-D Technologies Corp., Cutchogue, N.Y., USA, systems of this general type sometimes being referred to as "white light" digitizers. As compared with systems based on scanning lasers, "white light" digitizers offer significant advantages, including almost instantaneous operation and therefore the ability to effectively "freeze" the image of the foot and eliminate the effects of movement, greatly simplifying operation in a clinical environment. It will be understood, however, that in some embodiments other forms of three-dimensional imaging systems may be utilized in the imaging section of the apparatus, including but not limited to scanning laser systems, for example.

Figure 5:
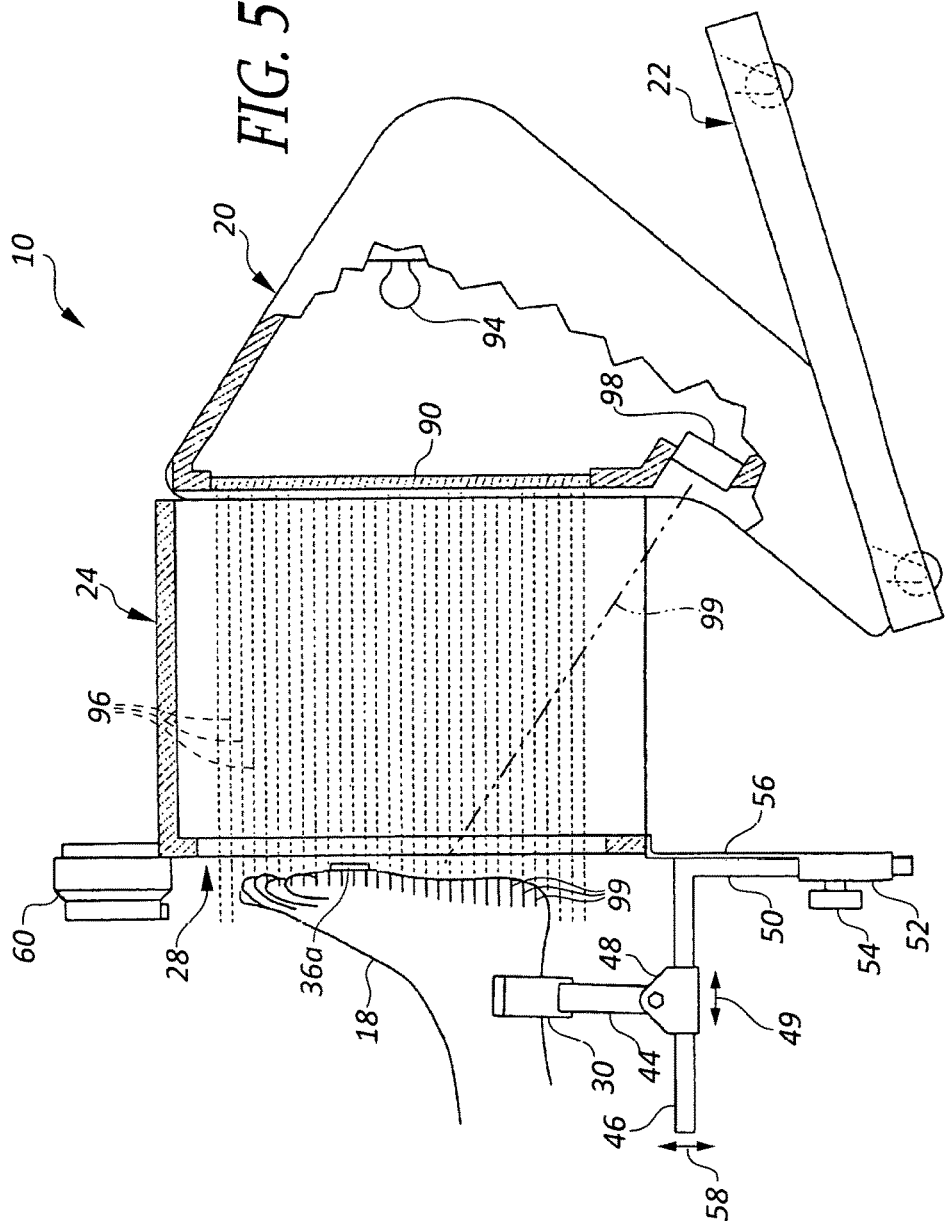
FIG. 5 is an enlarged side elevational view of the imaging apparatus of FIG. 1-3, partially in cutaway, showing the manner in which the optical imaging section of the apparatus projects a pattern of lines onto the plantar surface of the foot, that are viewed at an angle by a camera to determine the contours of the plantar surface.

Inasmuch as the "white light" three-dimensional digitizer alone is a more-or-less "off the shelf" component, its operation will be described herein only briefly. As is shown in FIG. 3, the digitizer employed in the illustrated embodiment includes a transparent or semi-transparent face plate 90 on which a series of opaque, parallel, transverse orientation lines 92 are formed. As can be seen in FIG. 5, a bulb 94 or other light source is positioned in the housing of the digitizer behind the faceplate 90, generally along an axis substantially perpendicular to the plantar surface of the foot 18. Operation of the light source 94 illuminates the plantar surface of the foot, with the images of the opaque lines 92 being projected against the plantar surface, as indicated by dotted lines 96, to create a corresponding pattern of lines 78 on the surface of the foot. The resulting image is captured by a camera 98 set to view the surface along an axis 99 a predetermined acute angle to the axis at which the pattern is projected onto the foot. Thus, although the lines 97 appear generally parallel as viewed along the projection axis from plate 90, the contours of the plantar surface of the foot cause the lines to deviate from parallel in the image that is captured by camera 98. The deviation from parallel, combined with the known angle between the axis of projection and the axis of the camera, and other factors, permits the contours of the foot to be accurately calculated by associated software, with the data being outputted in suitable digital form.

The data representing the contours of the patient's foot can therefore be obtained quickly and conveniently in a clinical environment using the apparatus of the present invention. The patient may be seated in a suitable chair and place his or her foot into the alignment section of the apparatus in the manner described and then push away, with the attendant clinician making minor adjustments as necessary and simply activating the switch to digitize the contours of the foot. Not only are clinical efficiency and patient comfort greatly enhanced, but the opportunities for error are greatly reduced as compared with prior techniques.

FIGS. 9-18 illustrate a second preferred embodiment of the present invention, which is generally similar to the embodiment described above in terms of overall operation and layout, but which differs somewhat in its carriage and alignment sections.

Figure 9:
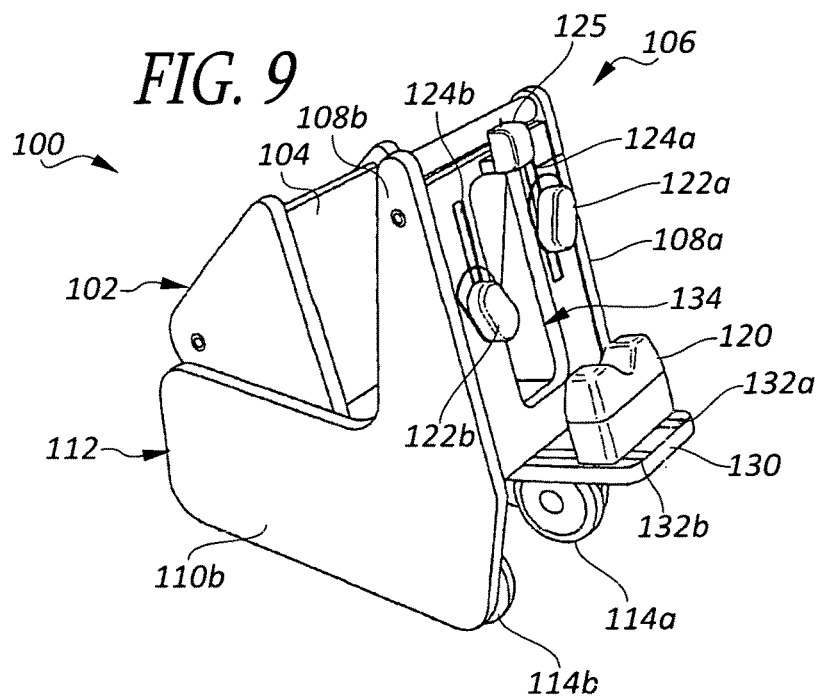
FIG. 9 is a perspective view of a foot imaging apparatus in accordance with another preferred embodiment of the present invention.

As can be seen in FIG. 9, the apparatus 100 includes an imaging section 102 that is substantially the same as described above and includes a face plate 104 for projecting a pattern of parallel lines onto the plantar surface of the foot. Rather than being supported on a box-like spacer frame, however, the alignment section 106 of the apparatus is supported on a pair of rigid flange portions 108a, 108b that extend upwardly from the sidewalls 110a, 110b of the wheeled chassis 112. Also, rather than the pivoting casters of the embodiment described above, the wheeled chassis includes a pair of horizontal axis wheels 114a, 114b on the trailing end disposed towards the patient, and a single ball transfer unit (ball roller) 116 on the opposite end that is free to roll in any direction; it will be understood that in some instances there may be multiple ball transfer units rather than the single unit that is shown. A particular advantage of the arrangement of wheels and ball transfer unit employed in chassis 112, as compared with conventional casters, is that this avoids the initial pivoting motion or "jog" that is created by the offset vertical axes of casters, which allows the apparatus to follow a comparatively smooth, unbroken arc as it moves away and pivots towards the centerline of the body as the patient's leg is extended, and which also facilitates free movement of the chassis in the transverse plane of the floor in order to perform adjustments as necessary.

Figure 10:
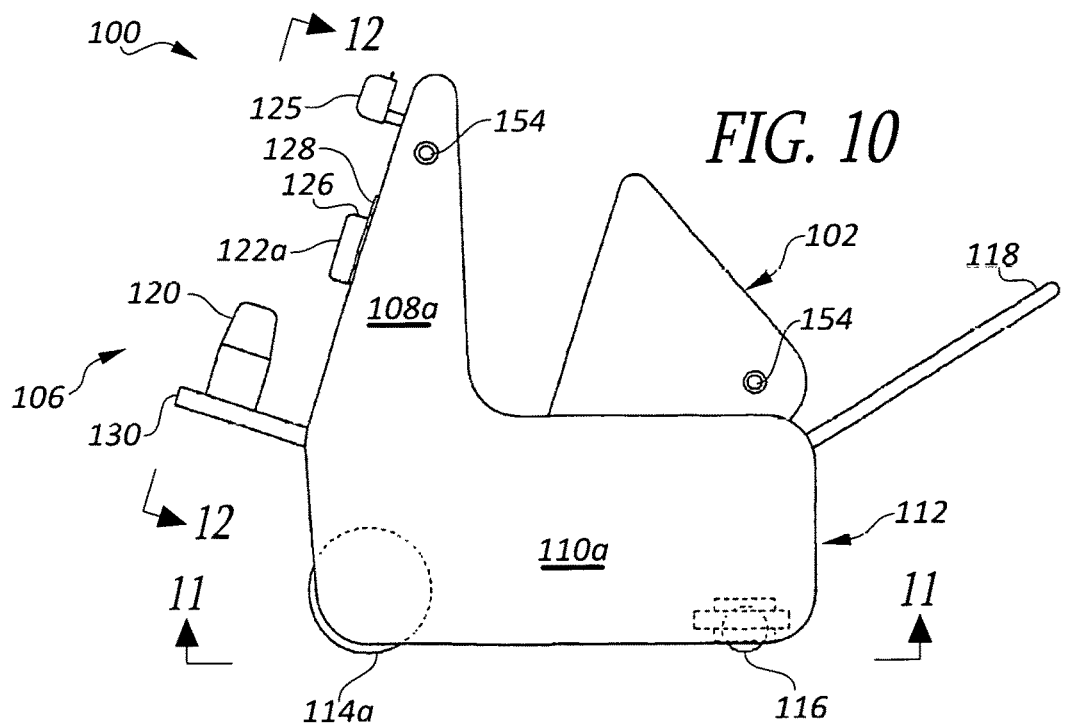
FIG. 10 is a side elevational view of the foot imaging apparatus of FIG. 9, showing the configuration and locations of the components thereof in greater detail.
Figure 11:
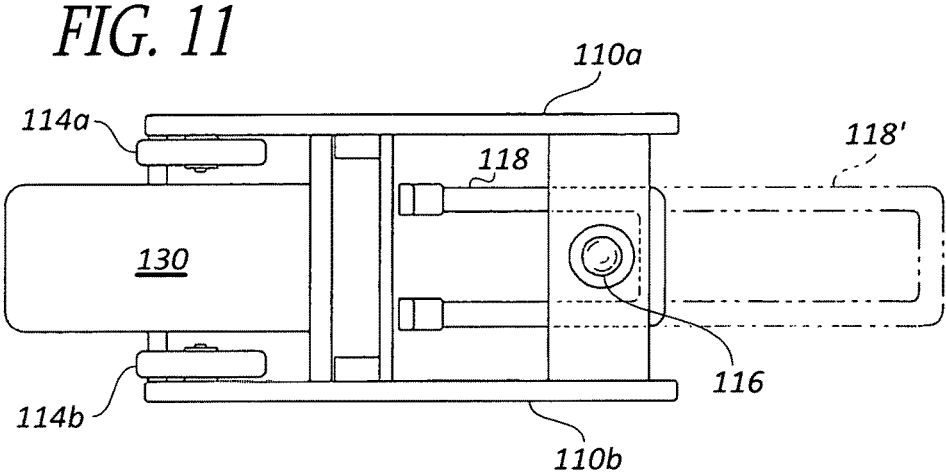
FIG. 11 is a bottom plan view of the apparatus of FIGS. 9-10, taken along line 11-11 in FIG. 10, showing the configuration of the wheeled chassis of the apparatus in greater detail.

As can be seen with further reference to FIG. 10 and also FIG. 11, the chassis 112 includes an optional extensible (e.g., telescoping) handle 118, on the side disposed away from the patient, both to provide an aid to the clinician in adjusting the position of the chassis and also to facilitate transportation of the assembly between locations, such as between examination rooms.

Figure 12:
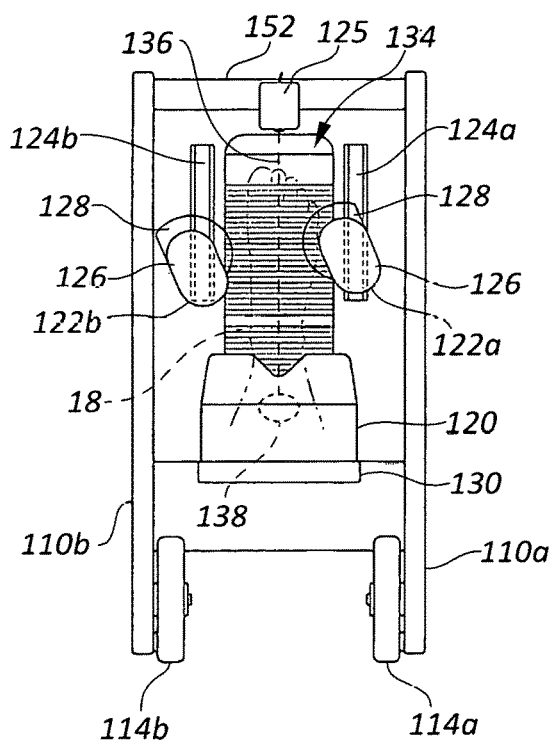
FIG. 12 is a rear elevational view of the apparatus of FIGS. 9-10, taken along line 12-12 in FIG. 10, showing the configuration of the alignment components of the apparatus in greater detail.

Referring again to FIGS. 9-10, it can be seen that the alignment section 106 of the embodiment illustrated therein includes a V-shaped heel saddle 120, right and left adjustable plantar support members 122a, 122b, and a laser pointer 125, that perform functions similarly to the corresponding elements described above. Rather than sliding bars, however, the adjustable support members 122a, 122b are rotatable units slidingly mounted in generally vertical channels 124a, 124b. As can better be seen in FIG. 12, the rotatable supports include hand grip portions 126, and inwardly disposed somewhat semicircular projecting flange portions 128 formed of a transparent material, similar to the transparent support pads described above. Thus, as can be seen in FIG. 12, the transparent support flanges 128 are positioned beneath fifth metatarsal areas of the feet simply by sliding the respective (right or left) support member 122a, 122b through its associated track to the general location and then rotating the flange inwardly, by turning handgrip 126. As can be seen the handgrips 126 preferably have an enlarged oval form, with the distance between the edge of the handle and the outer edge of the clear projecting flange 128 being selected such that the flange will be positioned beneath the fifth metatarsal head when the handle portion is moved to be adjacent or in contact with the side of the foot. The semi-circular shape of the transport flanges 28 in combination with the slide channels, also facilitates rapid and convenient positioning of the supports beneath the heads, so that this can be accomplished without excessive manipulation or "fiddling."

The V-shaped heel saddle 120, in turn, is supported on a platform 130 that projects towards the patient, in sliding engagement with a pair of tracks 132*a*, 132*b* that permit the stirrup to be moved towards or away from the aperture 134 in a manner similar to that described above, but with a simplified sliding motion. The sliding interfit between the tracks and the cooperating portions of the heel saddle 120 preferably includes a slight frictional resistance, as do tracks 124*a*, 124*b* and the cooperating portions of the adjustable members 122*a*, 122*b*, so that the members can be conveniently slid to the desired locations but will then remain in place without assistance once released. As with the heel stirrup described above, saddle 120 is centered on the central plane of the imaging section of the apparatus, as can be seen from its relationship to beam 136 and camera 138 in FIG. 12.

Use of the apparatus 100 and the manner in which it cooperates with a patient's foot and leg is generally similar to the embodiment described above, and is illustrated in FIGS. 13-18.

Figure 13:
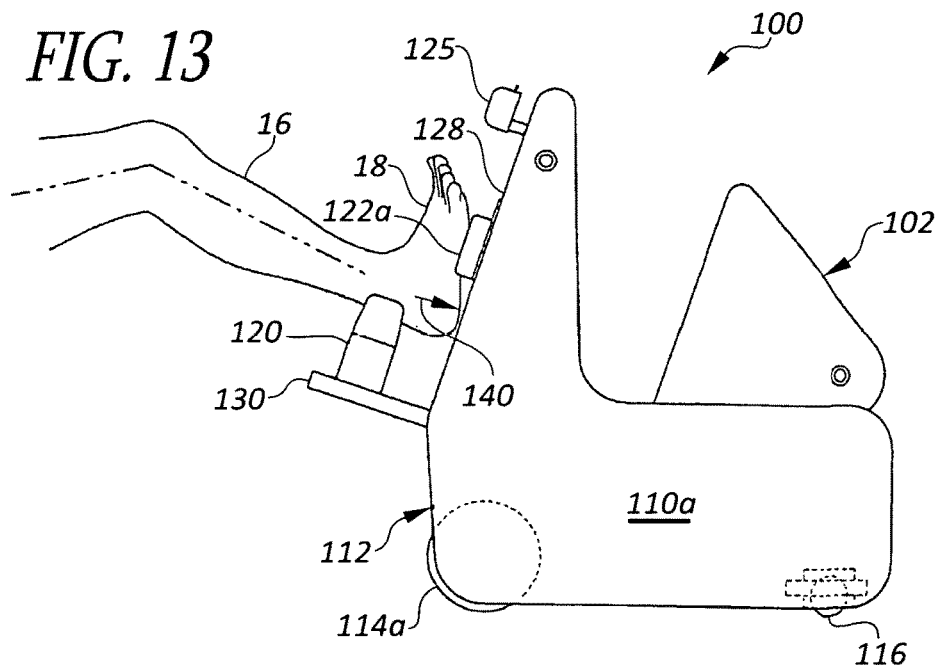
FIGS. 13-15 are sequential elevational, environmental views of the imaging apparatus of FIGS. 9-10 with a patient's foot placed therein, showing the manner in which the foot is set in the alignment section of the apparatus and the leg then extended and the ankle joint plantarflexed, similar to FIGS. 6-8.
Figure 14:
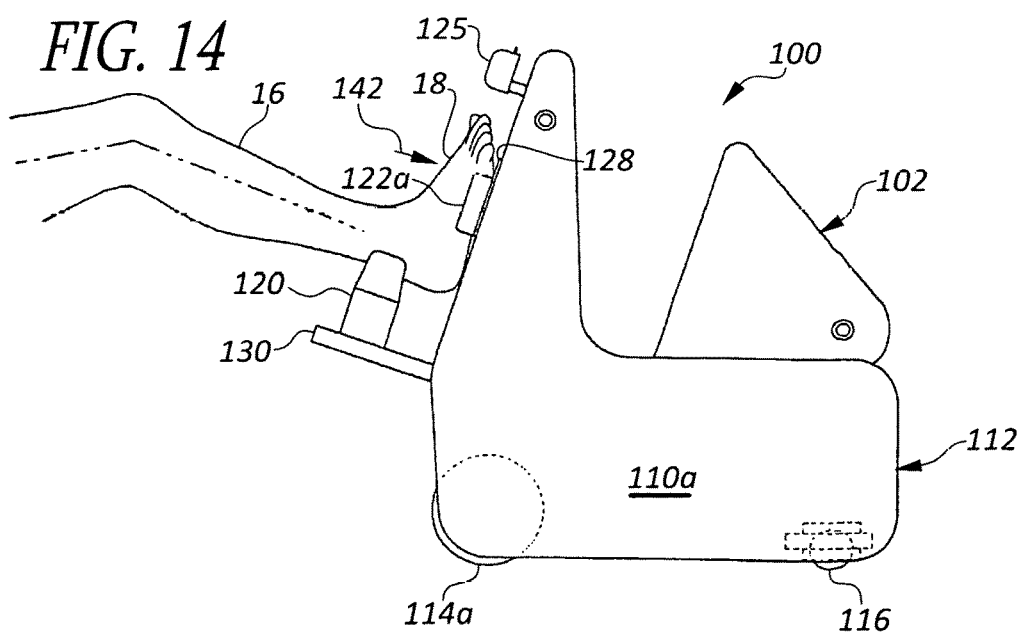
Figure 15:
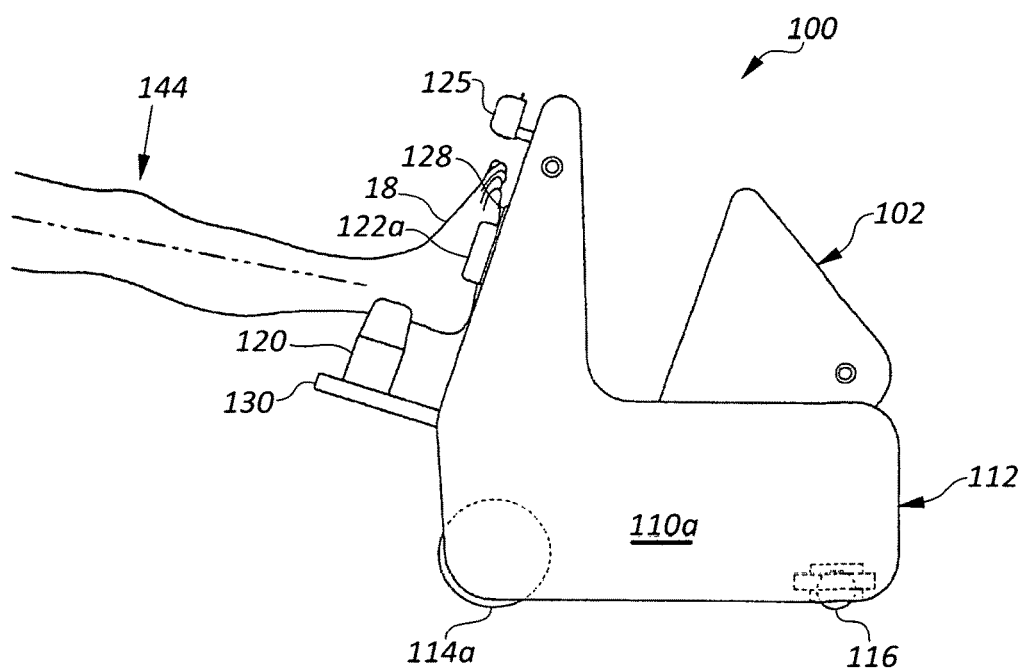

As can be seen in FIG. 13, the user's foot is first placed in the heel stirrup with the knee raised and the forefoot dorsiflexed and heel pressed forward, as indicated by arrow 140. The respective lateral forefoot support member 122*a*, 122*b* is adjusted into position along its track, and then rotated inwardly to move the clear support flange 128 thereof into the area beneath the fifth metatarsal head of the foot. The patient next relaxes the foot and allows the ankle to plantarflex the forefoot, as indicated by arrow 142, so that the fifth metatarsal head is subjected to a mild reactive force in the dorsal direction, mimicking the force of gravity so as to lock the midtarsal joint in the manner described above. The support member 122*a*/122*b* is then rotated inwardly/outwardly as needed in order to align the second metatarsal head of the forefoot with the centerline beam 134 projected by laser 125.

Figure 16:
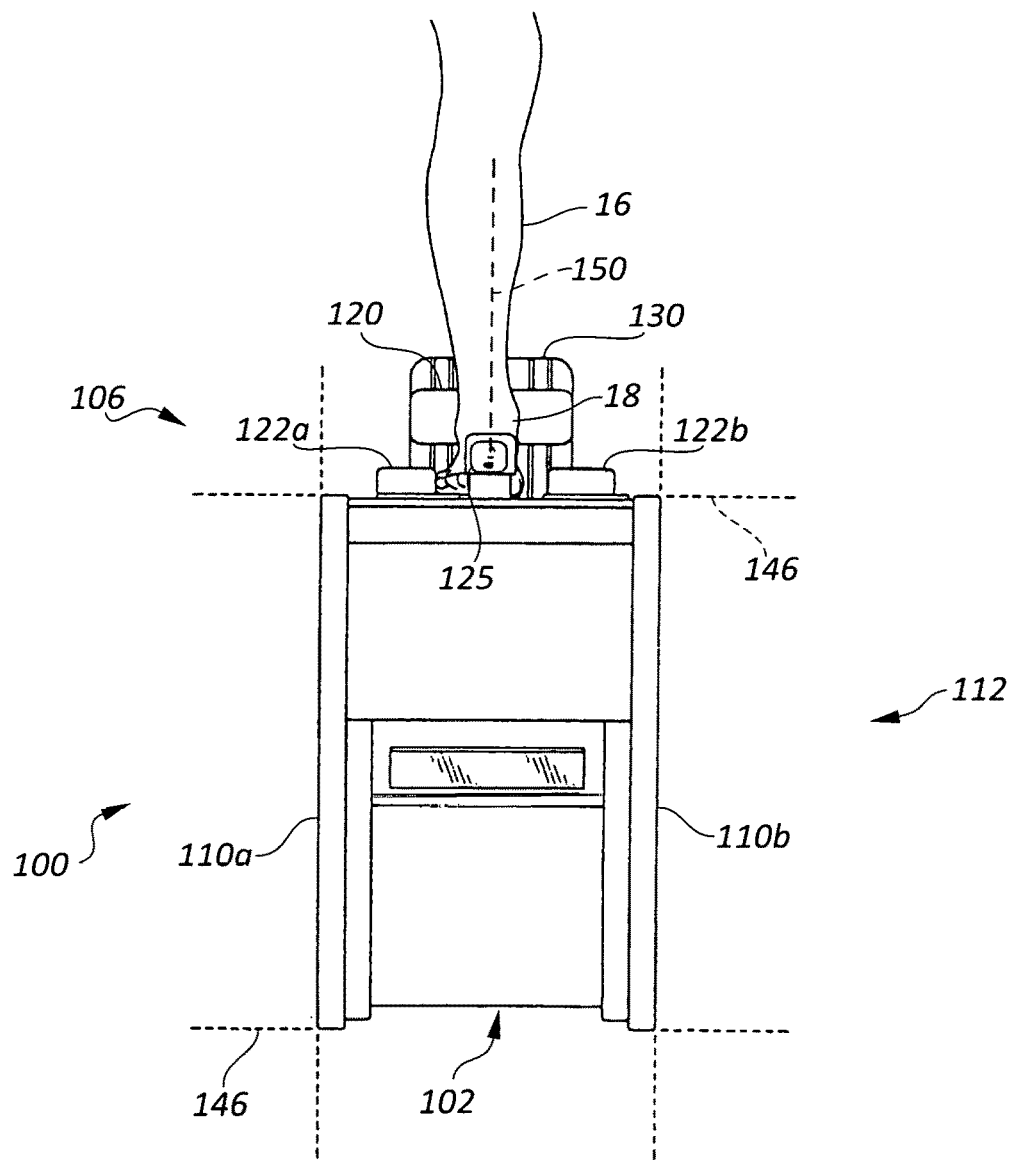
FIG. 16 is a first top plan, environmental view of the apparatus of FIGS. 9-10 with the patient's foot placed therein, in the position shown in FIG. 14 with the leg bent and the knee raised and with the ankle joint dorsiflexed.
Figure 17:
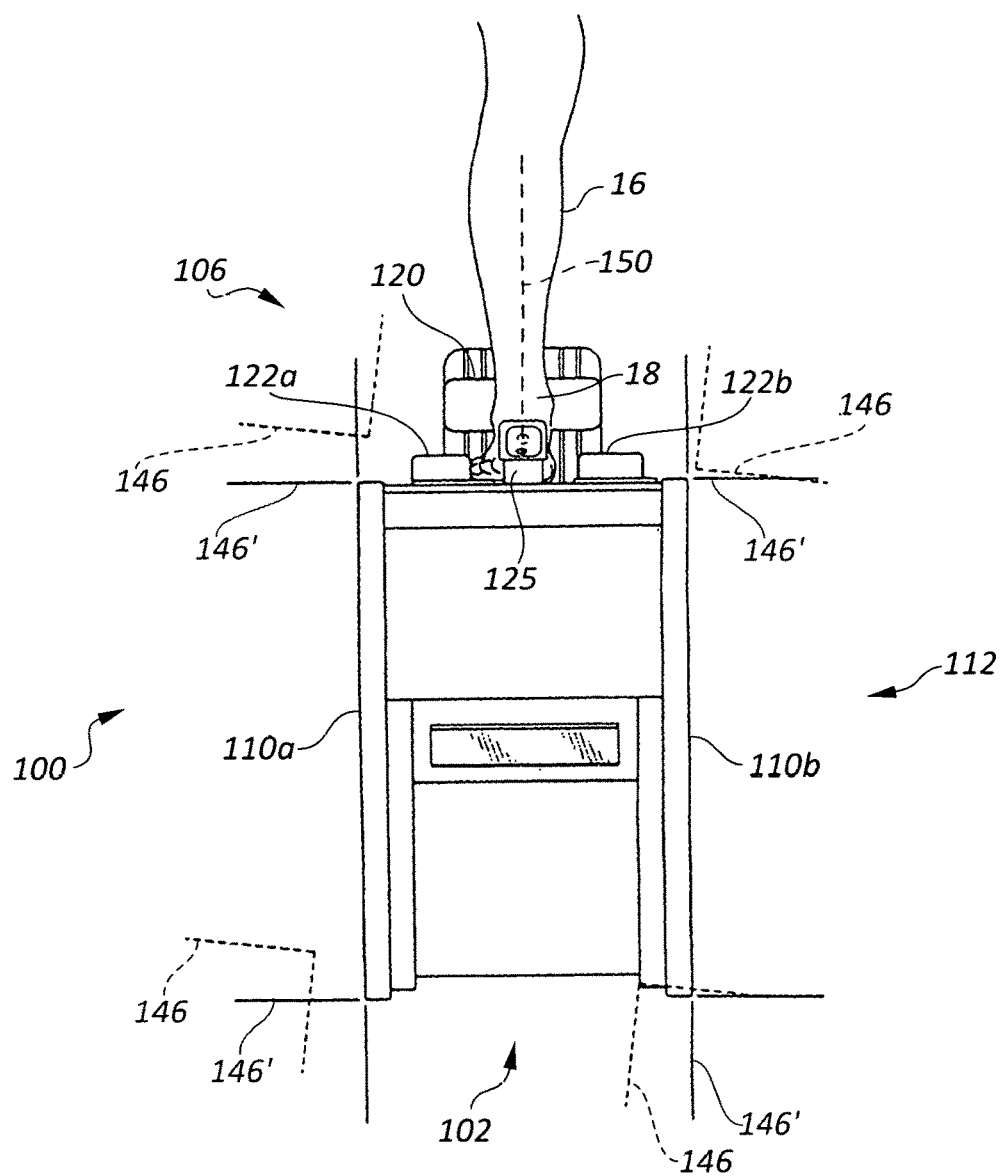
FIG. 17 is a second top plan, environment view of the apparatus of FIGS. 9-10 with the patient's foot placed therein, in the position shown in FIG. 16 with the ankle plantarflexed and the knee lowered and the leg extended so as to push the apparatus away from the patient.
Figure 18:
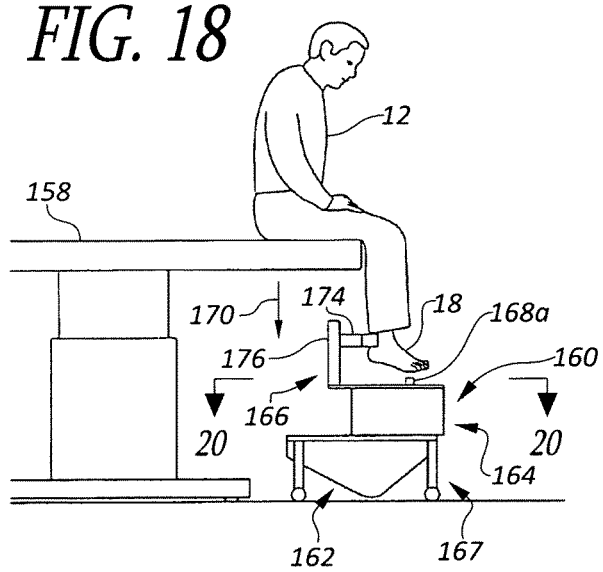
FIG. 18 is a side elevational, environmental view of a foot imaging apparatus in accordance with another embodiment of the present invention, in which the foot is moved vertically relative to the alignment section of the apparatus to reactively load the area of the fifth metatarsal head to lock the midtarsal joint, and the chassis of the apparatus is moved medially/laterally and/or proximally/distally as needed to align the foot and place the subtalar joint in a neutral condition.
Figure 19:
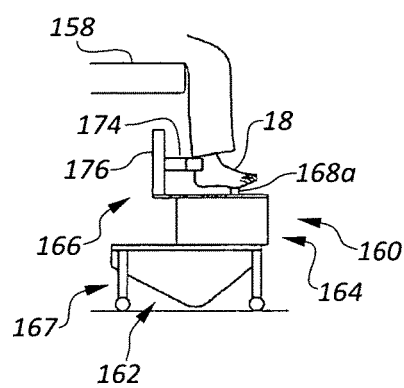
FIG. 19 is a second side elevational, environmental view of the foot imaging apparatus of FIG. 9, showing the position of the foot when it has been lowered onto the alignment section of the apparatus.

The patient then lowers the knee and extends the leg, as indicated by arrow 144 in FIG. 16, causing the apparatus to roll outwardly and turn inwardly (towards the patient's centerline), as can be seen by comparison of FIGS. 17-18. In particular, FIG. 17 shows the orientation of the apparatus 100 relative to the patient when in the position of FIG. 14, i.e., with the forefoot plantarflexed 90° to the lower leg but with the knee still raised; as can be seen therein, the apparatus, including its wheeled chassis at this point, lies in substantially coaxial alignment with the patient's lower leg and the associated side of the hip. However, as the patient lowers the knee and straightens the leg so as to push the apparatus away, the inward deviation of the lower leg causes the leading (distal) end of the apparatus to turn inwardly towards the centerline of the patient's body, as is indicated by the shift between the dotted and solid reference lines 146, 146' in FIGS. 17 and 18, allowing the second metatarsal head and distal one-third of the lower leg to come into alignment with one another and with the beam 150 projected by the laser 125. In short, as the patient pushes the apparatus away the wheeled chassis allows the apparatus, and in particular the central plane of the imaging section, to align itself with the distal one-third of the lower leg such that the subtalar joint is in the neutral position. Minor adjustments can then be made by the clinician if necessary, rotating the handgrip of the associated support and/or using handle 118 and also a crossbar 152 at the top of the alignment section. To move the foot into alignment with the center plane of the imaging section, as indicated by the beam 136 of the laser pointer passing over the second metatarsal head of the foot and onto the distal one-third of the lower leg; in so doing, the neutral position of the subtalar joint can be approximated/verified by the clinician manually rotating the lower leg internally and externally and observing the resultant movement of the laser beam 136, to one side and the other from alignment with the second metatarsal head and distal one-third of the lower leg. The image of the plantar surface of the foot is then captured for digitization by simply pressing one of the switches 154 that actuate the imaging section 102 of the apparatus.

It will be understood that in some cases or embodiments the dorsally-directed load may be applied to the area of the fifth metatarsal head in a direct manner, rather than by first setting the foot into the saddle or other support with the heel projected and then pantarflexing the forefoot onto the support as described. However, it has been found that such an approach generally leads to the ankle joint being in a plantarflexed position and the remainder of the foot in an inverted position relative to the transverse plane at the viewing area, and therefore less than optimal results when imaged. This problem is avoided by placing the foot/leg on the saddle with the ankle dorsiflexed and then plantarflexing the foot, in the manner that has been described.

The embodiments described above employ wheeled chassis to achieve relative movement between the patient and alignment section in order to position the foot with the midtarsal joint locked and the subtalar joint in the neutral position. FIGS. 18-22, in turn, illustrate an embodiment in which the patient's foot is lowered onto the support member of the apparatus in order to establish the requisite reactive force acting dorsally on the fifth metatarsal head.

Accordingly, as can be seen in FIG. 18, the patient 12 is seated on a vertically movable platform 158, such as an examination table for example, with the foot 18 positioned more-or-less directly over the apparatus 160. The apparatus 160 includes an imaging section 162 and spacer frame 164 similar to the corresponding components of the embodiment shown in FIGS. 1-2, and also an alignment section 166, all supported on a wheeled chassis 167. However, rather than moving horizontally to load the foot, the assembly remains in position on the floor as the patient is lowered to bring the fifth metatarsal head area of the foot into contact with the adjustable support 168, as indicated by arrow 170 in FIG. 18.

Since relative movement is provided by the table 158 or other vertically moveable support, the patient need not dorsiflex the foot before placing it in the apparatus; instead, the heel is simply positioned in the heel stirrup 174 and reactive force is generated as the fifth metatarsal head area of the foot comes into contact with and is then reactively lifted by the transparent pad 172 at the end of the support member 168*a*/168*b*; in so doing, the heel stirrup 174 is allowed to move vertically with the foot by the sliding engagement formed with its upwardly projecting support 176, similar to the stirrup 120 and support 130 described above. The position of the apparatus can then be adjusted in the transverse plane of the floor to place the subtalar joint in the neutral configuration and bring the foot into alignment, with the beam 178 of laser 180 aligned with the second metatarsal head and distal one-third of the lower leg, by moving the apparatus on the floor in the necessary direction or directions using wheeled chassis 167. It will be understood that relative vertical movement between the apparatus and the patient's foot may in some instances be established by raising the apparatus, or an operative portion thereof, relative to the patient's foot, rather than lowering the patient's foot onto the apparatus as shown.

Figure 20:
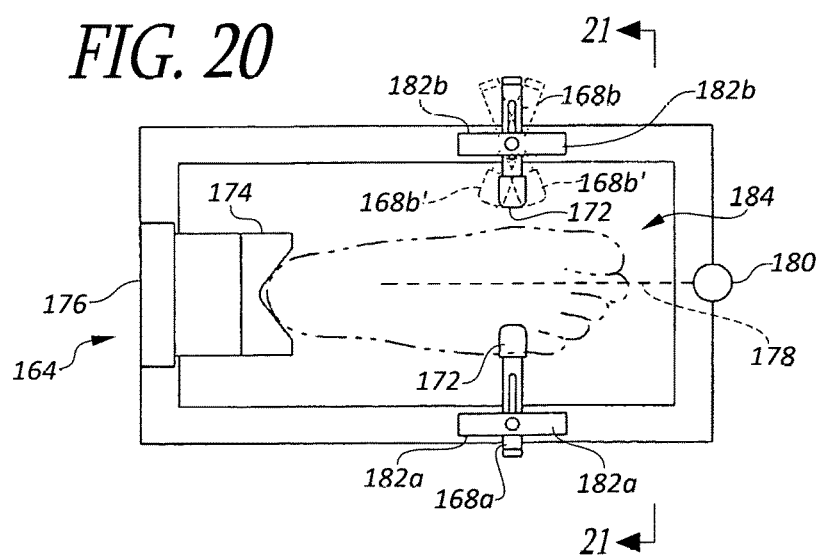
FIG. 20 is a plan view of the foot imaging apparatus of FIGS. 18-19, taken along line 20-20 in FIG. 18, showing the relationship of the foot to the alignment section and also to the aperture for the optical imaging section of the apparatus.
Figure 21:
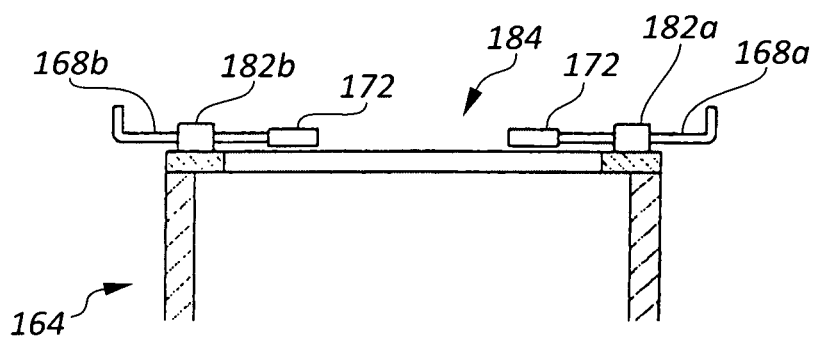
FIG. 21 is a cross-sectional view of the alignment section of the foot imaging apparatus of FIGS. 18-19, taken along line 21-21 in FIG. 20, showing the structure of the supports for reactively loading the fifth metatarsal head of the foot in greater detail.
Figure 22:
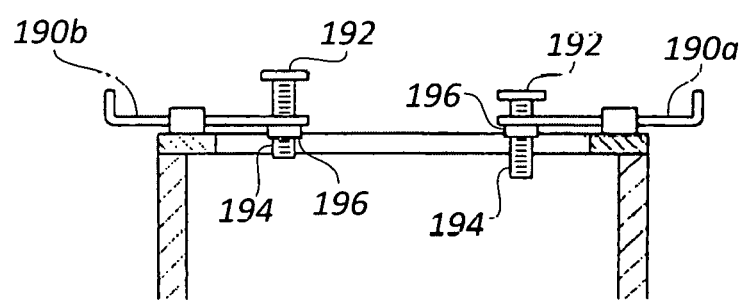
FIG. 22 is a cross-sectional view, similar to FIG. 21, of the alignment section of a foot imaging apparatus in accordance with another embodiment of the invention, in which the support members include adjustable height pads for engaging the fifth metatarsal head areas of the feet.

In the embodiment illustrated in FIGS. 18-21, the adjustable members are mounted for pivotable adjustment in brackets 182a, 182b at the sides of the aperture 184, as indicated by dotted line images 168a' and 168b' in FIG. 20 (see also FIG. 21). FIG. 22, in turn, shows an arrangement in which the alignment section includes adjustable supports 190a, 190b having head members 192 at their inboard ends that are vertically adjustable by means of shafts 194 that are in threaded engagement with cooperating nuts 196, to aid in adjusting the position of the plantar surface of the foot, and in particular with respect to the focal length of the camera of the imaging section. It will be understood that other forms of adjustable support members may occur to those skilled in the relevant art, and furthermore that although having the support members formed of a transparent material is preferable in terms of imaging accuracy, it is anticipated that in some instances opaque supports may be used instead and the obscured contours established by interpolation or other suitable means.

Figure 23:
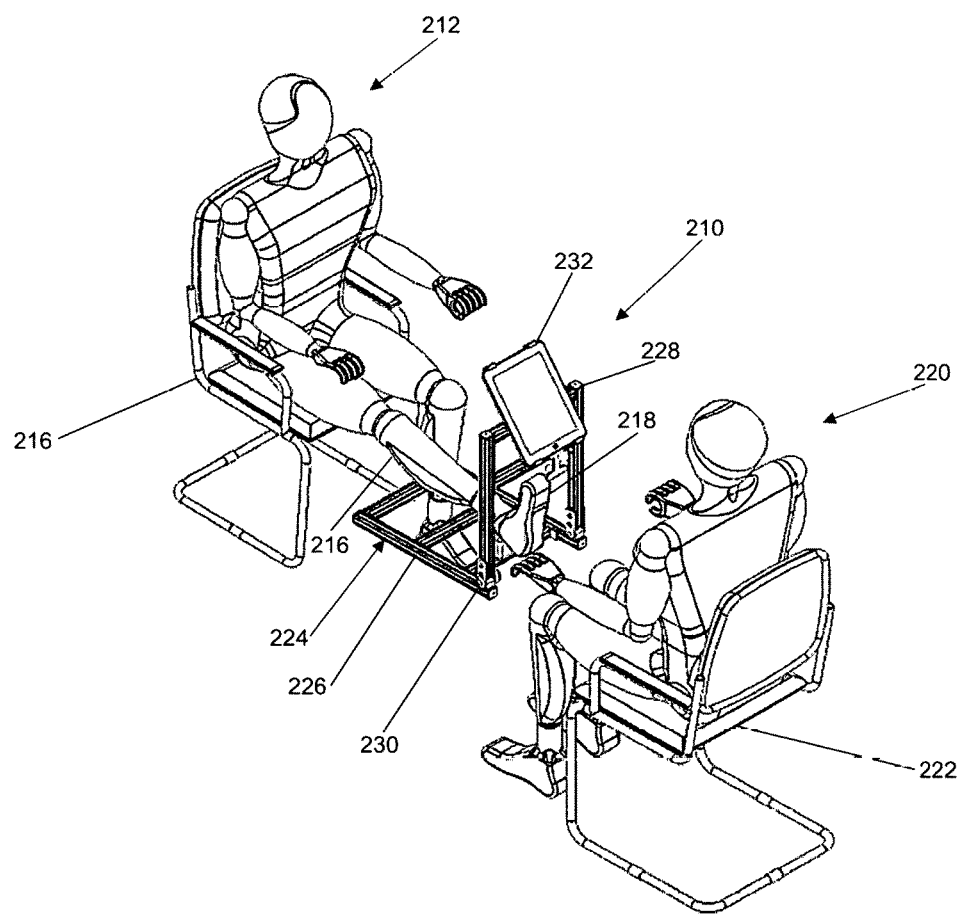
FIG. 23 is a perspective, environmental view of a portable foot imaging assembly in accordance with another embodiment of the present invention, showing the apparatus with the right foot of a patient placed therein in preparation for the contours thereof being digitized by a clinician seated opposite the patient.

FIG. 23 shows a lightweight portable foot imaging assembly 210 in accordance with another embodiment of the present invention. The apparatus is illustrated in use with a patient 212 seated on a chair 214 or other support, with a leg 216 outstretched to place the foot 218 in the imaging assembly, and an operator 220 seated on a second chair 222 or other support on a side opposite the patient so as to be in position to conveniently manipulate the patient's foot and operate the apparatus.

Figure 24:
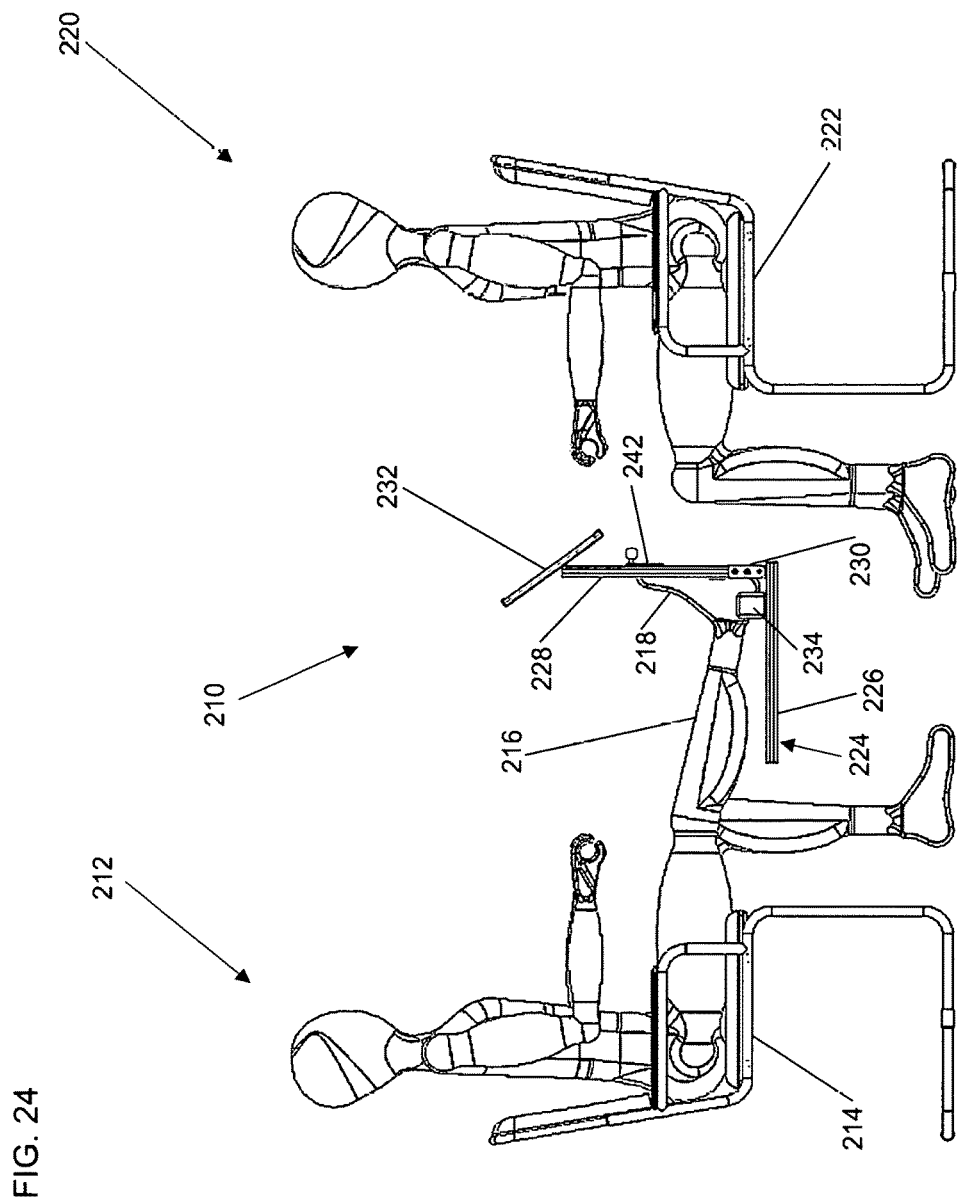
FIG. 24 is a side elevational, environmental view of the imaging assembly in use by a patient and operator as shown in FIG. 23, showing the relationship of the patient's foot and lower leg to the apparatus in greater detail.
Figure 25:
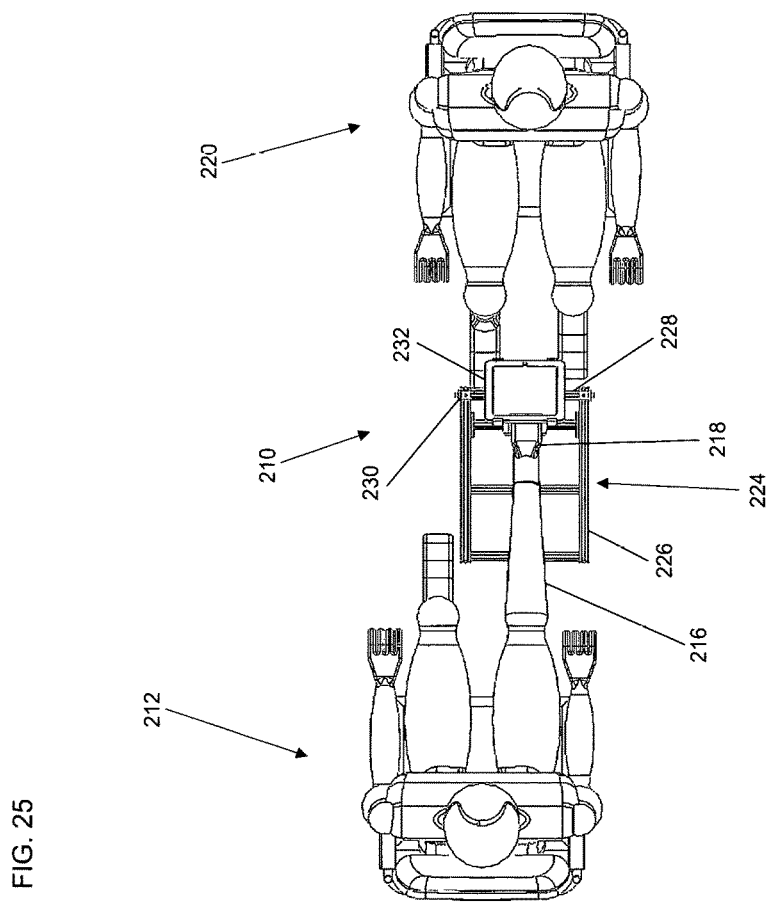
FIG. 25 is a top plan, environmental view of the imaging assembly and patient and operator of FIGS. 23-24, showing the alignment of the patient's lower leg and foot with the apparatus and digitizer in greater detail.

As can be seen with further reference to FIG. 23 and also FIGS. 24-25, the portable imaging assembly 210 includes a folding frame 224 having horizontal and upright sections 226, 228 joined by hinge connections 30. The hinge connections permit the operator to transition the frame assembly 224 between a collapsed form for transportation/storage and the erected, operational configuration shown in FIGS. 24-25, as will be described in greater detail below.

Figure 26:
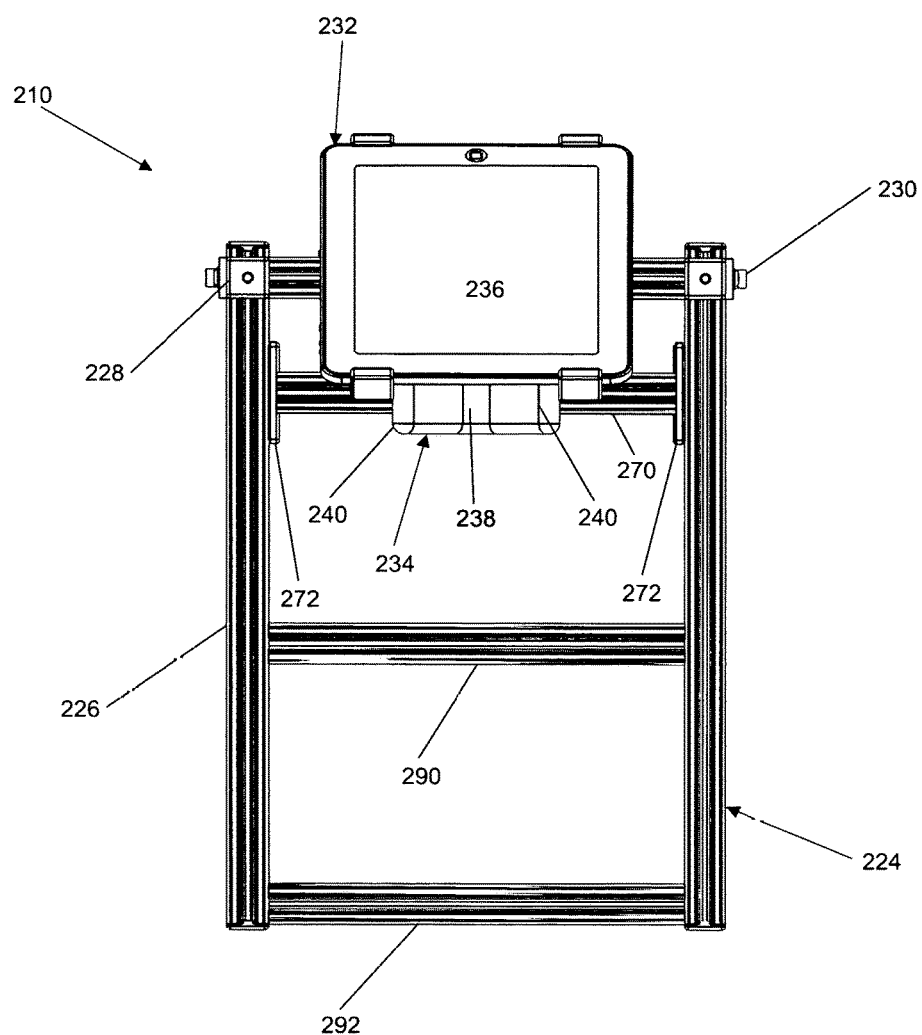
FIG. 26 is a top plan view of the imaging assembly of FIGS. 23-25, showing the frame assembly of the apparatus with an exemplary portable imaging device mounted thereon.
Figures 27A, 27B:
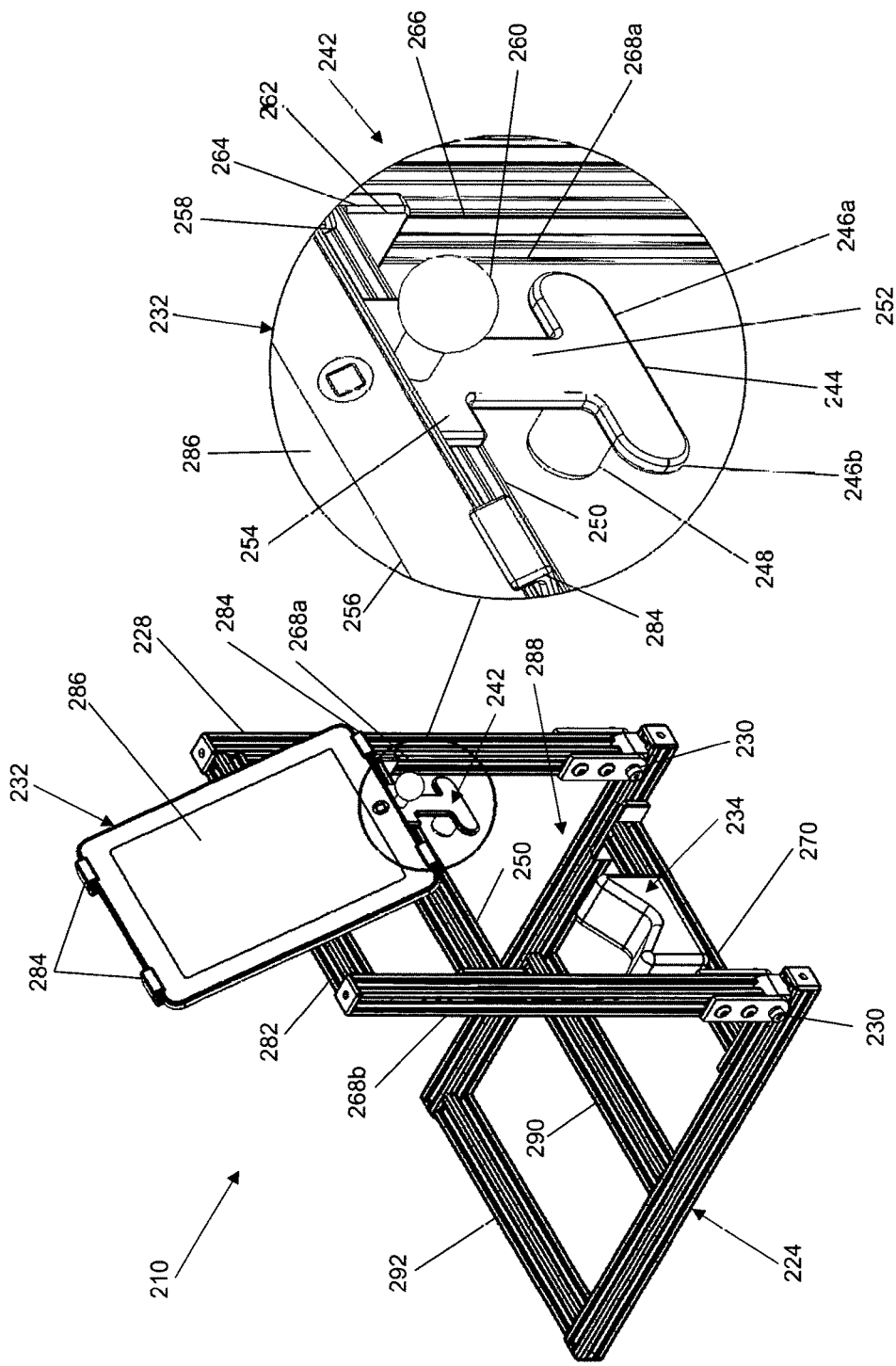
FIG. 27A is a front/operator side perspective view of the imaging assembly of FIG. 26, showing the components of the assembly in greater detail.
FIG. 27B is a partial, enlarged perspective view of the metatarsal head support mechanism of the imaging assembly of FIG. 27A, that is positionable for use with both left and right feet.
Figure 32:
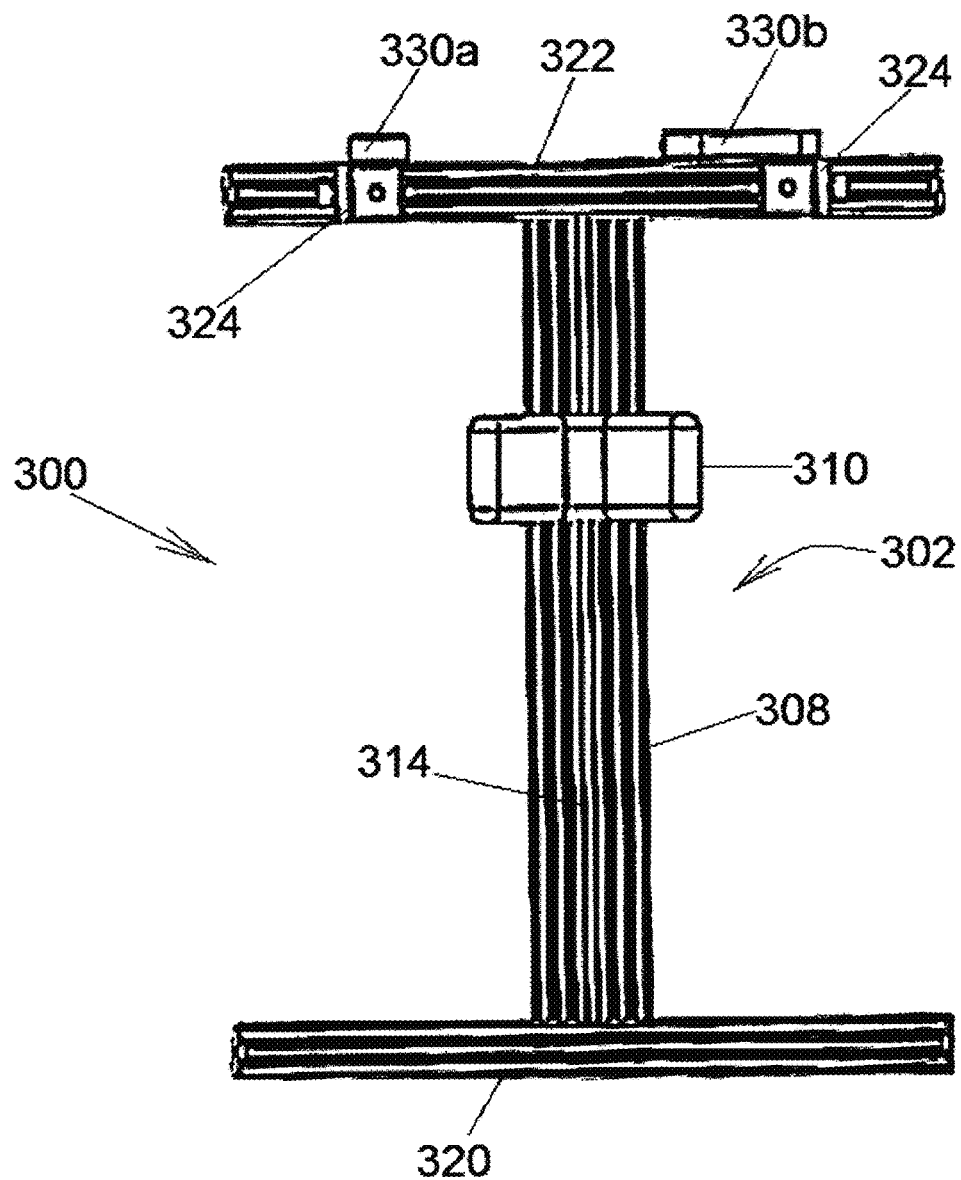
FIG. 32 is top plan view of the imaging assembly of FIG. 30A, showing the relationship of the members of the frame sections and other components of the assembly in greater detail.

A digital imaging device 232, such as a tablet computer equipped with a camera and suitable software, is detachably mounted proximate the top of the upright section 228 and may be angled towards the operator 220 for convenient viewing and use by the latter. As can be seen with further reference to FIG. 24 and also FIG. 26, a rearfoot cradle or saddle 234 is in turn mounted to the horizontal lower frame section 226 generally distal of the patient 212. In the illustrated embodiment, the rearfoot cradle 234 is centered on the longitudinal axis of the lower frame section 226 and includes a channel-shaped recess that aligns the foot and leg longitudinally in the frame assembly and is preferably cushioned or otherwise surfaced to support the patient's foot/lower leg in comfort while holding it firmly in position. In the illustrated embodiment the recess is somewhat V-shaped, having first and second angled side walls 236 that slope downwardly to form a channel 238 and that are bounded on their outer sides by bolsters 240; it will be understood, however, that various other contours that engage and support and stabilize the foot and lower leg may be employed as well.

A metatarsal head support assembly 242 is mounted to the upright section 228 of frame 224 so as to be positioned above and distally of (relative to the patient) the rearfoot cradle 234 when the assembly is erected. As can be seen in FIGS. 27A-27B and 28A-28B, the metatarsal head support assembly 242 includes a depending plate 244 having right and left tabs or flanges 246a, 246b that form support surfaces which extend generally perpendicular to the centerline of the saddle 234, on either side of a stop member 248 that projects generally longitudinally from the plate in a direction towards the patient. The flanges 246a, 246b form individual metatarsal head support members that respectively engage the lateral forefoot areas of the right and left feet of the patient, to exert a dorsally directed force that "locks" the foot in position for imaging.

Plate 244 positions the flanges 246a, 246b a spaced distance below a crossbar 250 of the upright section 228 of the frame assembly so as to provide clearance between the crossbar and the toes and forefoot, so that the contact with the foot that generates the dorsally directed force is limited to the areas beneath fifth and fourth metatarsal heads and preferably to the fifth metatarsal head alone. In the illustrated embodiment, plate 244 has a somewhat "inverted-T" configuration with a vertical central stem 252 that supports the flanges 246a-b below the crossbar, however, it will be understood that structures having various other shapes may be employed to support the tabs or other support members in position, such as suitably configured arms, rods or brackets, for example. Furthermore, the tabs or other support members may be supported individually rather than sharing a common support as in the illustrated embodiment.

As can be seen with further reference to FIGS. 27A-27B and 28A-28B, the upper end 254 of plate 244 is mounted to a guide member 256 that is in sliding engagement with a cooperating track-shaped channel 258 formed in crossbar 250, the guide member suitably being formed of a rigid, low-friction material such as molded nylon for example. A knob 260 mounted to the upper end of plate 244 projects towards the position of the operator, so as to form a handle that permits the operator to slide the support assembly 242 in left and right directions in a convenient manner. The ends of the horizontal crossbar 250 include brackets 262 having additional guide members 262 that are in turn received in sliding engagement in track-shaped channels 66 formed in the vertical frame members 68a-b of the upright frame section. The operator is thus able to also adjust the vertical position of the support assembly 242 by grasping knob 266 and applying force in an upward or downward direction as appropriate.

Similarly, the lower crossbar 270, to which the heel cradle 234 that engages to foot is mounted, includes end brackets 272 having guide members 274 that are slidingly received in longitudinal tracks 276 in the frame members 278a, 278b of the horizontal frame section 226. Crossbar 270 is thus selectively slidable in a longitudinal direction within the horizontal frame section 226 so that the operator is able to adjust the position of the foot and lower leg away from and towards the metatarsal head support assembly 242 on the upright frame section, as will be described in greater detail below. The sliding rearfoot support provides advantages in terms of ease of use and control, however, other embodiments may employ other mechanisms to provide relative movement between the foot and metatarsal head support members; for example, the frame assembly may include or rest on a base having skids or wheels to permit the operator to slide or roll the apparatus towards and away from the patient, or the chair or other support for the patient may be provided with wheels or otherwise be moveable towards and away from the apparatus while the latter remains stationary.

The guide pieces mounted to ends of the crossbars 250, 270 of the frame assembly are preferably formed of a durable, low-friction material that forms a stable sliding engagement with the guide tracks in the frame bars; for example, the guide pieces may be formed of nylon, UHMWPE, or similar material extruded to have a suitable profile and cut to length. The frame members, in turn, may suitably be formed of extruded aluminum alloy or other rigid, preferably lightweight material having a profile including the longitudinal guide track that receives the guide pieces, cut to length and assembled into the frame. It will be understood, however, that other forms of construction may be employed in various embodiments, such as assemblies using molded or machined/milled components, for example.

When in use, assembly 210 may be positioned in front of the patient, with the lower leg and foot extended and resting on the assembly as shown in FIGS. 23-25. The crossbar 270 and saddle 234 are initially pushed back from the upright section of the frame so as to be located generally towards the patient, leaving the foot free to relax and plantarflex. With the foot thus generally in position, and using the laser pointer or other light projection device (when included) to establish alignment, the operator slides crossbar 250 up or down within the upright frame section and slides the metatarsal support assembly 242 left or right along the crossbar so as to position the appropriate support flange 246*a*/246*b* on the lateral side of the foot beneath the area of the metatarsal head.

For example, FIGS. 23-25 show the right foot being imaged. In this case, the operator slides the metatarsal support assembly 242 to the operator's left, so that from the patient's view the support assembly is positioned to the side of the right foot and then draws the support assembly back towards the centerline so as to move flange 246*a* to a position beneath the dorsal surface of the fifth metatarsal head. As this is done, the projecting stop piece 248 comes up against the lateral side of the foot so as to arrest the assembly at the point where the support flange extends beneath only the fifth metatarsal head, and not further across the foot. With the support flange thus correctly positioned, the operator draws the crossbar 270 of the lower, horizontal frame section in a plantar direction (i.e., away from the patient), so that with the resulting movement of the foot the stationary support tab reacts against the fifth metatarsal head to generate a dorsally-directed force, that causes the midtarsal joint to "lock" and maintain the foot in the desired configuration for imaging to determine the relevant contours. The electronic device 232 that is employed to obtain the digital images themselves may suitably be a portable tablet computer, camera or similar device, equipped with camera functions and appropriate software for capturing digital images of the foot that can be processed to determine the contours thereof. In the illustrated examples, the imaging device may be a portable tablet computer, such as an Apple™ iPad™ or iPhone™, loaded with Autodesk™, 123Catch™ or a similar app. For example, in a preferred embodiment the imaging device may suitably be an Apple™, iPad™ Air™ equipped with a plug-in Structure IO™ sensor (http://structure.io) that performs 3D capture of the foot, the Apple™ iOS™, SDK and structure.io SDK being employed to provide a user interface and capture format appropriate to imaging of the foot and associated areas of the anatomy for the intended purposes. A bracket 280 (see FIG. 28A) may be mounted to the upper crossbar 282 of the upright section 228 of the frame, with upper and lower sets of clips 284 that engage corresponding edges of the device so as to angle the screen 286 for convenient viewing and use by the operator.

In addition, as noted above, a laser pointer or other light-projecting device may be mounted to the crossbar or elsewhere on the frame, to project a visual reference line onto the foot and/or leg in order to assist in aligning the foot for imaging. In particular, the patient's foot and leg may be positioned so that the line projected by the laser lines up with the second metatarsal head and ray of the foot and the distal one-third of the anterior section of the leg, in order to insure that the subtalar joint is in the neutral condition for imaging of the foot. It will be understood that in addition to a laser other forms of alignment aids may be employed, such as other types of light-projecting devices, optical and digital imaging devices and markers, rods or other physical guides for example.

To perform the 3D capture, the operator may remove the tablet or other imaging device 232 from bracket 280, for example by sliding it out of clips 284, and then position the device so that the lens is directed towards the subject area from the desired angles. For example, the lens of the imaging device may be directed towards the plantar surface of the foot through the open area 288 below bar 250 and the operator may shift the position and/or angle of the device to capture multiple images as necessary or desirable for accurate determination of the contours in the relevant areas. Inasmuch as the only contact is the support tab in the area beneath the fifth metatarsal head, substantially the entirety of the plantar surface of the foot is exposed to unobstructed viewing by the imaging device. Furthermore, the operator may move the device around to the open sides of the frame assembly to obtain unobstructed images of the sides and top of the foot and of the ankle and lower leg, as may be needed to determine the contours of these areas for types of orthotic devices that engage these parts of the anatomy; for example, the contours of the upper side of the foot and those of the ankle and lower leg may be imaged for use in the making of an ankle-foot orthotic.

In the illustrated embodiment, the imaging device is a handheld unit that the operator moves manually about the areas of the foot to capture the images, which greatly contributes to the portable, flexible and economical nature of the apparatus. It will be understood, however, that in some embodiments the tablet, camera or other imaging device may be mounted on an adjustable support, such as an articulated arm for example, that allows it to be moved into position and then left there without having to be held by the operator, and furthermore that in some embodiments movement of the imaging device may be automated in part or in whole. Similarly, it will be understood that while the arrangement of manually slideable crossbars in the illustrated embodiment provide significant advantages in terms of weight, portability and cost, it will be understood that some embodiments may employ other structures or mechanisms for sliding or otherwise adjusting the positions of the metatarsal head and rear foot support members, such as longitudinal tracks, rails or rods, for example, and furthermore that movement of the supports may in some embodiments be automated and/or accomplished mechanically, electrically, hydraulically or pneumatically, as by electromechanical gear or screw-drive mechanisms or pneumatic pistons, for example.

When the assembly is in the erected configuration, hinges 30 arrest the upright section 228 of the frame in a generally vertical orientation, at a right angle (approximately 90°) to the horizontal frame section 226 in the illustrated embodiment, with the sections being held in position by friction or by a releasable lock or locks at the hinges, for example. Then, to collapse the assembly, the operator pivots the upright and horizontal sections 228, 226 towards one another about hinges 230, so that the frame assembly 224 collapses to the configuration shown in FIGS. 29A-29C. As noted above, the side and cross members 268a-b, 250, 282 of the upright frame section are constructed of pieces of stock, suitably formed of extruded aluminum or other rigid, preferably lightweight material, cut to length and assembled in a common plane; side members 278a-b and sliding and fixed cross members 270 and 290-292 are likewise formed of pieces of stock and assembled to construct the horizontal frame section 262. When collapsed, the two generally planar frame sections 228, 226 thus lie flat against one another to create a thin and compact form that is easily carried and stored, either by itself or within a cooperating case or carrier.

By way of illustration, example dimensions for an assembly constructed in accordance with the illustrated embodiment using approximately 1-inch square extruded aluminum are set forth in the following table, making reference to the reference letters in FIGS. 29A-29C.

| EXAMPLE DIMENSIONS | |
|---|---|
| "a" | 17 inches |
| "b" | 12 inches |
| "c" | 3.3 inches |

It will be understood that the dimensions set forth in the above table are provided by way of example rather than limitation, and may vary depending on design factors.

FIGS. 30A-32 show a portable foot imaging apparatus 300 in accordance with second embodiment of the present invention, having a frame assembly 302 that features a somewhat simplified form of construction.

Similar to the embodiment described above, frame assembly 302 includes horizontal and upright sections 304, 306, joined by hinges 308 at a position distal from the patient. The frame sections are again suitably constructed of pieces of extruded material, however, rather than two parallel side members, horizontal frame section 304 includes a single, central longitudinal member 308 that supports the rearfoot saddle 310 for movement towards and section 306. As can be seen in FIG. 12A, the rearfoot saddle is mounted atop a somewhat M-shaped bracket 312 having a depending central guide leg that rides within an upwardly facing centerline-channel 314 in frame member 308, and depending outer legs having inwardly projecting end members formed of low-friction material that engage additional, horizontal channels 316 in the sides of the frame member. Transverse crossbars 320, 322 are mounted at the ends of the longitudinal frame member for stabilizing the assembly atop a support surface, with crossbar 322 also supporting the upright section 106 of the frame on hinges 324. FIG. 34B provides an enlarged view of one of the hinges 324 as mounted to crossbar 322.

The upright frame section 306 of the frame assembly in turn includes first and second side members 326a, 326b, joined by a cross member 328 at the end opposite hinges 324. A reference beam laser and a bracket to hold an imaging device may be mounted to the upper cross member 328 in a manner similar to that described above.

The members of the upright frame section 306 are thus arranged in a rectangular fashion about an opening 340 that provides an unobstructed view of the plantar surface of the foot, similar to opening 188 described above. By comparison with the above embodiment, however, the apparatus 300 in FIGS. 30A-32 employs separate left and right pivotable metatarsal head support members 330a, 330b, rather than a pair of support members mounted together in a single horizontally sliding assembly. The pivoting support members are individually mounted to the frame members 326a, 326b at the sides of the upright frame section 106 on pivot pins 332 formed by the protruding ends of T-nuts, the heads of the T-nuts being captured in sliding engagement by guide channels 334 in the sides of the frame members that face towards the operator.

To employ the apparatus when erected, the operator places the patient's foot in the rear foot saddle 310 in a manner similar to that described above, and selects the corresponding metatarsal support member, i.e., support member 330a for the left foot and support member 330b for the right foot. Then, with the foot generally in position, the operator slides the selected metatarsal support member vertically within the guide channel of the associated frame member 326a, 326b, and pivots the end of the support member inwardly towards the centerline of the assembly, so as to position the tab-shaped end of the support in the area beneath the fifth metatarsal head of the foot. The operator then slides the rear foot saddle 310 towards the upright frame section so as to draw the metatarsal head area against the cooperating surface of the support, generating a dorsally-directed force to resistance against the fifth metatarsal head of the foot and thereby placing the foot in a locked condition. Images of the plantar surface of the foot may then be captured through opening 340 in the manner described above, with the top of the foot and the ankle and lower leg likewise being open for unobstructed imaging around the sides of the frame.

When not in use, the operator may collapse the frame assembly to a compact configuration for transportation and/or storage by pivoting the frame sections 304, 306 towards one another about hinges 324 so that the two frame sections lie generally flat against one another in a stacked relationship. Although the illustrated embodiment is intended to be portable so as to provide the benefits noted above, it is envisioned that in some instances the assembly may be mounted or otherwise fixed in place on a permanent or semi-permanent basis. FIGS. 8-11 show additional aspects and optional components of the assemblies described above.

Figure 33:
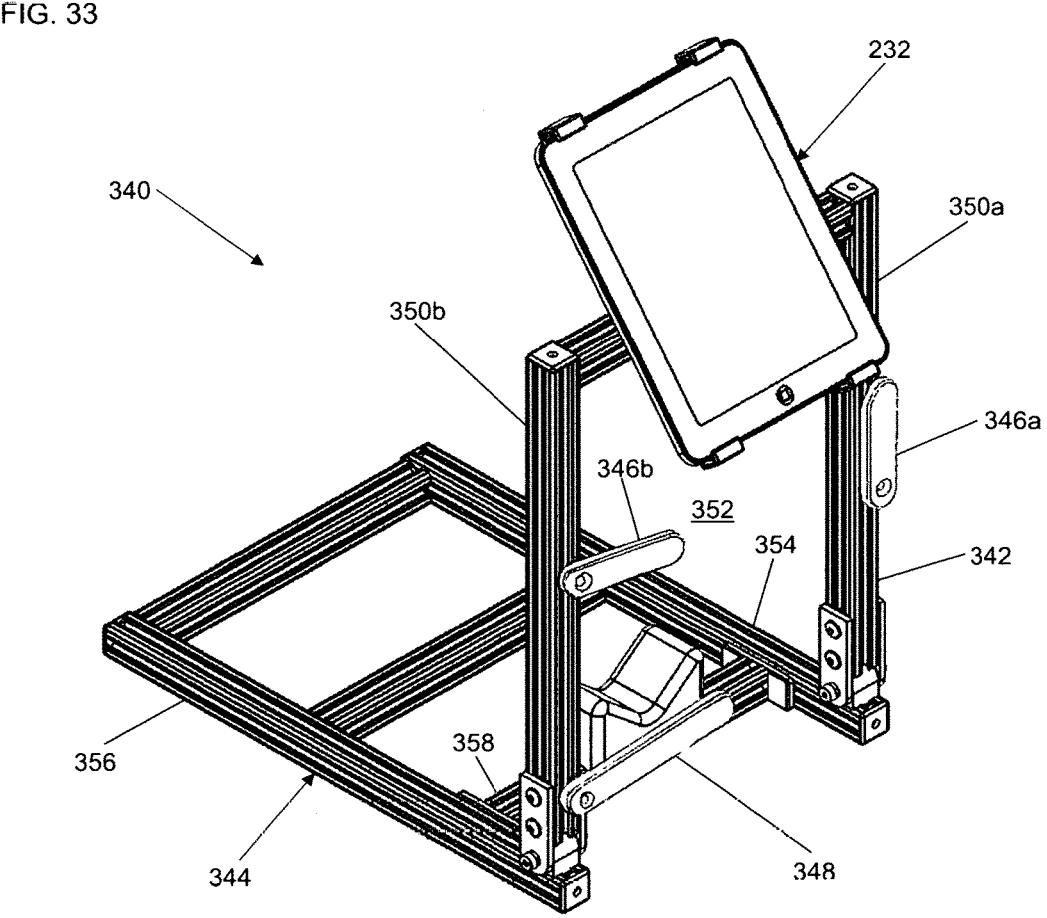
FIG. 33 is a perspective view of a foot imaging assembly similar to that of FIG. 26, including an optional heel support member that contacts the heel of the patient's foot so that in cooperation with the metatarsal head support member the lower leg and foot are positioned at an approximate 90° relationship in the assembly.

FIG. 33 shows a portable imaging assembly 340 having an upright section 342 of the frame 344 having in addition to the metatarsal head support members 346a-b and heel support member 348a. A third support member 348 that engages the plantar surface of the heel. Similar to the metatarsal head support members, the heel support member 348 is pivotally mounted to one of the upright frame members 350a-b for adjustable movement and extends into the opening of the upright frame section, but at a lower height corresponding to that of the heel. The function of the heel support member is to place the leg and foot in an initial orientation of approximately 90° with the fifth metatarsal head in contact with one of the metatarsal head support members, after which the foot is allowed to plantarflex so as to reactively load the fifth metatarsal head in a dorsal direction. Similar to the metatarsal head support members, it will be understood that the heel support member may have other configurations and forms of support within or outside of the frame.

With the heel support member 348 installed, the operator places the patient's foot in the heel engagement member 354 of the horizontal frame section 356 and extends the heel support in the opening 352. Using sliding cross-member 358 and with the foot and lower leg aligned as described above, the operator brings the foot into position so that the plantar surface of the heel is in contact with support member 348, preferably in the area directly beneath the calcaneous. The support surface of the heel support member 348 is in the same generally vertical plane as the corresponding surfaces of metatarsal head support members 346a-b, which is at a right angle to the plane of the horizontal frame section 356, so that when the heel is in contact with the heel support member 348 and the fifth metatarsal head of the foot is in contact with one of the metatarsal head support members 346a-b the foot and lower leg are positioned approximately 90° to one another.

The approximate 90° relationship is optimal for measurement for several purposes, owing to this being the approximate relationship of the foot and leg when the patient is standing upright. From this position the foot is allowed to plantarflex, i.e., in a direction away from the patient's body. As this occurs the metatarsal head support member 346a/346b remains stationary, holding the fifth metatarsal head against plantarflexing together with the rest of the foot and thus reactively loading the fifth metatarsal head in a dorsal direction and locking the midtarsal joint as described above. For many practitioners, therefore, the inclusion of the heel support member may improve the convenience, accuracy and repeatability of the procedure.

Figure 34A:
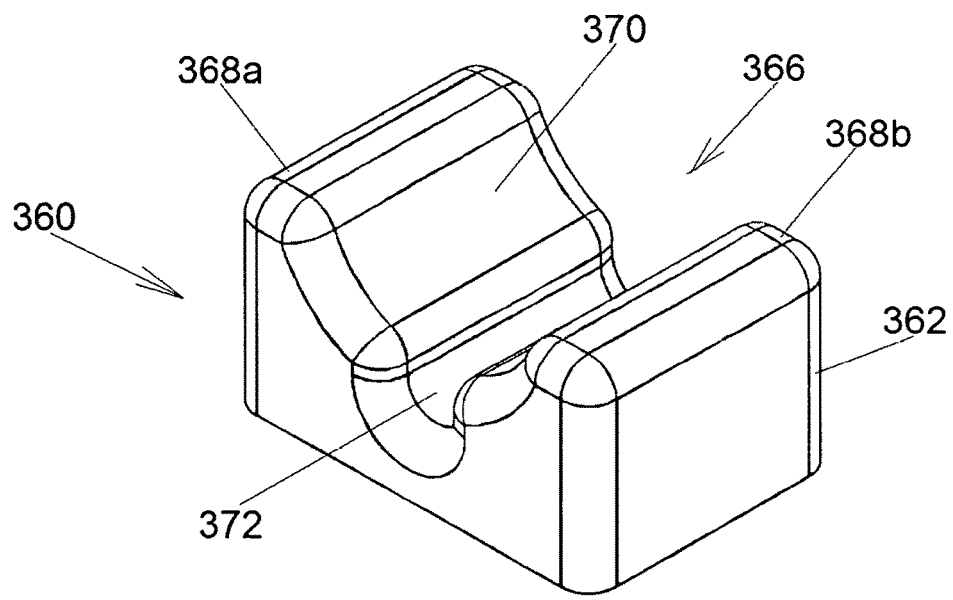
FIGS. 34A-34B are, respectively, perspective and end elevational views of a preferred form the rearfoot engagement member for use in the imaging assembly of FIG. 26, showing in detail the channel that receives the Achilles tendon of the patient's lower leg when set therein.
Figure 34B:
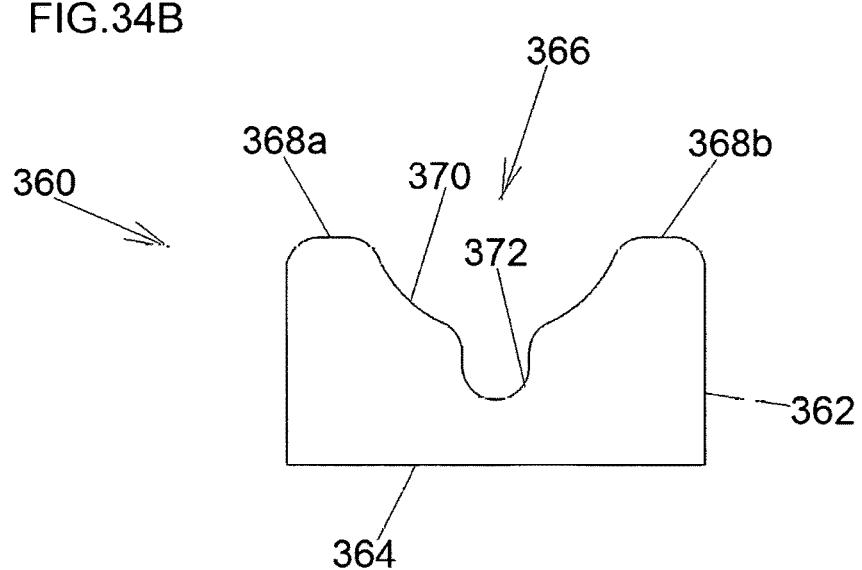

FIGS. 34A-34B show a rearfoot saddle member 360, that as compared with the rearfoot saddle member described above is particularly configured to engage and support an area of the rearfoot generally above the heel and behind the ankle.

As can be seen, the rearfoot saddle member 360 includes a somewhat block-shaped body 362 having a base 364 that is mounted to the front-to-rear sliding support of the frame assembly, e.g., crossbar 70 in FIG. 4 or sliding bracket 312 in FIG. 30A. The upper side of the saddle member includes a channel 366 bordered on the left and right sides by upstanding bolster portions 368a, 368b that fit against the medial and lateral sides of the rearfoot/lower leg. Channel 366 has a stepped inside contour, with a broader upper channel portion 370 and a lower channel portion 372 dipping downwardly in the middle of the former, both channel portions extending in a front-to-back longitudinal direction. The upper channel portion 370 has a relatively open, somewhat semi-cylindrical contour that is configured and sized to receive and comfortably support the broader areas of muscle and tissue in the area region behind the ankle, while the lower channel portion 372 is narrower and has a pronounced downward U-shape to accommodate the Achilles tendon with the sides of the lower channel portion engaging the sides of the tendon.

The engagement that is thus formed the rearfoot, and with the comparatively stiff, longitudinally extending Achilles tendon in particular, holds the foot and lower leg against rocking side-to-side or otherwise moving, consequently helping to stabilize the foot within the imaging assembly. The firm engagement that is established above the heel also permits the operator to draw the foot and lower leg into position in a positive manner, with a reduced tendency of the rearfoot to slide front-to-back as this is done. The channel portions may be tapered or otherwise contoured on one end or the other to provide a closer fit, and they may also more fully enclose the rearfoot area to provide an even firmer engagement. Similar to that described above, rearfoot saddle 360 may suitably be formed or covered with a firm yet resilient cushioning material for patient comfort.

Figure 35A:
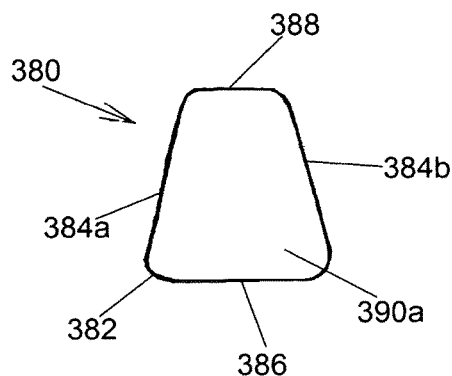
FIGS. 35A-35B are, respectively, outer and inner end elevational views of an angled dorsiflextion member that is optionally mountable to a metatarsal head support member of the assembly of FIG. 26 to dorsiflex the large toe of the foot opposite the fifth metatarsal head.
Figure 35B:
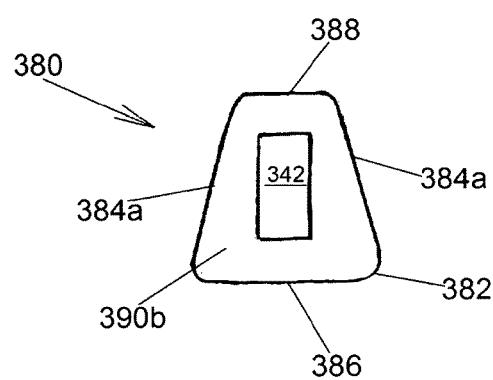
Figure 36:
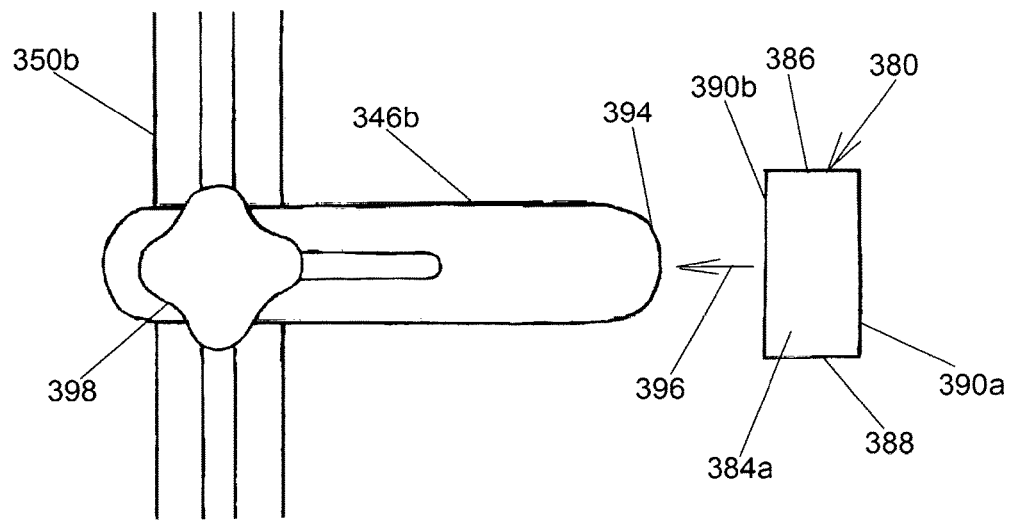
FIG. 36 is a front elevational view of one of the metatarsal head support members of the assembly of FIG. 26 together with the angled dorsiflextion member of FIGS. 35A-35B, showing the manner in which the latter is detachably mountable on the end of the metatarsal head support member for dorsiflextion of the large toe.

FIGS. 35A-35B and 36 show large toe dorsiflexion member 380, that may optionally be included in the assembly to dorsiflex the large toe at the same time as the fifth metatarsal head is being dorsiflexed by the metatarsal head support member on the opposite side. Simultaneous dorsiflexion of the large toe may be desirable for certain measurements based on conditions of the foot or practitioner preferences. Dorsiflexion member 380 dorsiflexes the toe itself rather than the first metatarsal head of the foot.

As can be see with reference to FIGS. 10A-10B, the large toe dorsiflexion member 380 includes a body 382 having first and second angled surfaces 384a and 384b. In the illustrated embodiment, body 382 is somewhat triangular in overall form, two sloped surfaces 384a, 384b arranged generally symmetrically about a vertical axis of the body and upper and lower ends 386, 388. As can be seen in FIG. 11, the angled faces 384a and 384b are preferably sized to contact the plantar surface of the large toe, with dimensions of about ¾ inch wide and 1¾ inch long being generally suitable.

As can be seen with further reference to FIGS. 10A-10B, at least one of the end faces 390a, 390b includes a socket 392 that corresponds in cross-section to metatarsal head support members 346a-b. To install the optional large toe dorsiflexion member the operator slides the dorsiflexion member onto the metatarsal head support member on the side of the foot opposite the fifth metatarsal head so that the end 394 of the support member enters socket 392, in the direction indicated by arrow 396 in FIG. 11. The dorsiflexion member is temporarily retained on the end of the metatarsal head support member, suitably by friction, and the operator then adjusts the vertical and horizontal position of the dorsiflexion member to be positioned beneath the plantar surface of the large toe. Once in place, the operator tightens the adjustment knob 398 to lock the metatarsal head support member and associated dorsiflexion member in location. Dorsally directed force between the toe and dorsiflexion member thus dorsiflexes the large toe to an angle corresponding to that of the angled surface 384a/384b, suitably about 15° from the vertical axis.

When finished, the large toe dorsiflexion member may be removed and stored, or installed on the opposite metatarsal head support member with the other angled surface 384a/384b facing towards the patient for use with the other foot. It will be understood that in some instances the large toe dorsiflexion member may be permanently installed or may be provided with its own support, rather than being removably installable on the metatarsal head support members as in the illustrated embodiment.

The contour data obtained using the frame assembly and electronic device may be supplied directly or indirectly to systems that perform actual making of the orthotic device, for example via email or other suitable forms of electronic transmission when obtained at a remote location. Manipulation of the data to create corresponding contours appropriate for the orthotic device may be performed using either the source or receiving system or a system elsewhere, and may include adjustment of contours based on corrections that are to be applied to the foot and other factors. For example, in the case of a shoe insert that cooperates with the plantar surface of the foot, corrections may be applied to the contours of the insert to adjust the angle of the rearfoot so as to improve the functions of the foot as it proceeds through the gait cycle. In another example, the orthotic device may be an ankle-foot orthotic constructed using contour data from images captured of the upper areas of the foot together with areas of the ankle and lower leg. The contour information may be supplied to the equipment that shapes the orthotic device accordingly, such as a CNC milling machine or an adjustable element mold assembly, for example.

In addition to external contours, the image data may be employed to calculate the volume of the subject area when the foot is in an optimized condition. As noted above, the apparatus enables images to be captured not only of the plantar surface, but also of the sides and upper surface of the foot and of the associated ankle and lower leg. The contours about the entire exterior of these areas may therefore be determined and hence the internal volume that is defined by the contours.

The volume is significant not just for construction of orthotic devices per se, but also for construction and use of such devices in conjunction with shoes and other articles of footwear. In general (with the exception of certain open top footwear), a finite volume is available within a shoe between the insole and the upper, which volume is occupied by the foot of the wearer. When an orthotic device is placed in the shoe, such as an orthotic insert that rests atop the insole, this consumes a portion of the volume that could otherwise be occupied by the foot. Moreover, people's feet vary tremendously in actual volume, even if they are nominally the same in terms of length and width, while ready-made shoes are generally constructed to have a volume that is based on some model or average. If insufficient volume is available due to the presence of an orthotic insert or to variation in foot shape then the shoes will fit too tight, resulting in discomfort and friction as well as potentially interfering with the ability of the foot to function biomechanically within the shoe (e.g., the ability to pronate and elongate so as to transition between flexible adapter and rigid lever states). As a result, the tendency amongst consumers is to purchase overly large shoes so as to avoid any possibility of a tight fit, but this in turn leads to a sloppy fit that presents problems of its own in terms of comfort and efficiency.

The ability to determine the volume of the individual foot when properly configured, as made possible by the present invention, allows the final fit to be optimized so as to avoid the problems of overly tight or sloppy fit. For example, if an individual is to be fitted with an orthotic shoe insert then the foot may be imaged for volume as described above and the volume of the insert also determined or measured, with the combined volume being compared with a measured or known volume of the intended shoe to evaluate the resultant fit; if too loose, a thicker, larger insert having a greater volume may be selected or made or a shoe having a smaller interior may be chosen, and vice versa. The shoe and insert may therefore function in combination to provide an optimal fit for the particular foot. Furthermore, the volume measurement may be determined and/or employed for different segments or different purposes over the length of the foot; for example, a volume measurement of the arch segment of the foot may be employed to create an orthotic insert that will provide a maximum amount of support in this area without causing excessive pressure between the shoe and the top of the foot. In another aspect, the measured volume of the foot may be employed, as well as the contours obtained from the imaging, to construct a custom shoe having an interior that is tailored to provide a close but not overly tight fit with the foot.

In addition to shoes, certain orthotic devices fit around or otherwise enclose areas of the foot and/or ankle and lower leg, such that the volume of that area is a significant factor for proper construction and operation of the device. For example, an ankle foot orthotic (sometimes referred to as an "AFO") commonly engages the lower leg, ankle and upper portion of the foot, from the front and back and both sides. A close fit is frequently required due to the degree of control that needs to be exercised as well as the comparatively high loading that the device will experience during use, as well as for reasons of comfort and avoiding friction/abrasion. Consequently, construction of AFOs frequently requires painstaking casting and molding steps similar to those described above, with the resulting drawbacks, and even if performed correctly the resulting device may be plagued by gaps or irregularities that compromise its function. By the present invention, however, both the external contours and the volume of the relevant areas of the leg, ankle and foot may be determined with a high degree of accuracy, and employed to construct an AFO or other orthotic device having a precise but not overly tight fit. For example, the contour and volume information may be used to construct an AFO in two or more pieces that when assembled together fit closely against all sides of the relevant parts of the anatomy without the presence of significant gaps or undesirable pressure areas.

In addition to imaging, the support and alignment system of the present invention may in some instances be utilized to hold the foot/leg in the correct functional position for more traditional measurement or construction processes, such as for wrapping and application of plaster-of-paris for the purpose of creating a positive mold from which an orthotic device can be constructed; similarly, it is envisioned that the system may be used to position the foot and leg for direct molding of a device, as by direct application of a pliable thermoplastic material, for example.

It is to be recognized that various alterations, modifications, and/or additions may be introduced into the constructions and arrangements of parts described above without departing from the spirit or ambit of the present invention as defined by the appended claims.

What is claimed is:

1. An apparatus for use in determining contours of a foot and/or an associated ankle and lower leg of a patient, said apparatus comprising:
   a support and alignment assembly that orientates said foot for imaging, said support and alignment assembly comprising:
      at least one metatarsal head support member that engages a plantar surface of said foot substantially only beneath a lateral forefoot area of said foot; and
      a mechanism that provides movement of said lateral forefoot area of said foot relative to said at least one metatarsal head support member so that said lateral forefoot area of said foot is reactively loaded in a dorsal direction by said at least one support member so as to lock a midtarsal joint of said foot.

2. The apparatus of claim 1, further comprising:
   an imaging device that captures an image of at least one subject area of said foot and/or said associated ankle and lower leg so as to determine contours of said subject area with said midtarsal joint of said foot locked.

3. The apparatus of claim 2, wherein said imaging device comprises:
   a handheld imaging device that is freely moveable by an operator to capture images of subject areas over a bottom and top of said foot and said associated ankle and lower leg of said patient.

4. The apparatus of claim 1, wherein said at least one metatarsal head support member comprises:
   at least one support member that engages said plantar surface of said foot substantially only beneath an area of said fourth and fifth metatarsal heads of said foot.

5. The apparatus of claim 4, wherein said at least one metatarsal head support member comprises:

a metatarsal head support member that engages said plantar surface of said foot substantially only beneath said fifth metatarsal head of said foot.

6. The apparatus of claim 1, wherein said mechanism that provides movement of said lateral forefoot area of said foot relative to said at least one metatarsal head support member comprises:
a foot engagement member that supports a rearfoot portion of said foot and a distal aspect of said associated leg and that is mounted for selective movement relative to said at least one metatarsal head support member.

7. The apparatus of claim 6, wherein said foot engagement member comprises:
a cradle that engages a rearfoot portion of said patient's foot and that is translatable towards and away from said at least metatarsal head support member.

8. The apparatus of claim 1, wherein said mechanism that provides movement of said lateral forefoot area of said foot relative to said at least one metatarsal head support member comprises:
a base on said support and alignment assembly that is adapted for manual movement of said assembly towards and away from said patient.

9. The apparatus of claim 6, wherein said support and alignment assembly comprises:
a collapsible frame having an erected configuration for use and a collapsed configuration for transportation or storage.

10. The apparatus of claim 9, wherein said collapsible frame of said support and alignment assembly comprises:
an upright frame section;
a horizontal frame section having the foot engagement member mounted thereon; and
at least one hinge interconnecting said upright and horizontal frame sections so that said frame sections are selectively pivotable apart to said erected configuration for use and to said collapsed configuration for transportation or storage.

11. The apparatus of claim 10, wherein said upright section of said frame comprises:
open end and side areas that expose plantar, side and upper surfaces of said foot for imaging by a portable imaging device.

12. The apparatus of claim 10, wherein said at least one metatarsal head support member comprises:
at least one metatarsal head support member that is adjustable vertically on said upright section of said frame assembly for use with longer and shorter feet.

13. The apparatus of claim 10, wherein said at least one metatarsal head support member comprises:
at least one metatarsal head support member that is adjustable laterally on said upright section of said frame assembly for use with wider and narrower feet.

14. The apparatus of claim 10, wherein said at least one metatarsal head support member comprises:
first and second metatarsal head support members mounted to said upright section of said frame assembly for use with right and left feet.

15. The apparatus of claim 14, wherein said first and second metatarsal head support members comprise:
first and second metatarsal head support members mounted on opposite sides of said upright section of said frame assembly for use with right and left feet.

16. The apparatus of claim 14, wherein said first and second metatarsal head support members comprise:
first and second support members slidingly mounted as an opposing pair to said upright section of said frame assembly so as to be movable between opposite sides of said frame assembly for use with right and left feet.

17. A method for determining contours of a foot and/or an associated ankle and lower leg of a patient, said method comprising the steps of:
providing at least one metatarsal head support member that engages a plantar surface of said foot substantially only beneath a lateral forefoot area of said foot;
moving said lateral forefoot area of said foot relative to said at least one metatarsal head support member so that said lateral forefoot area of said foot is reactively loaded in a dorsal direction by a said at least one support member so as to lock a midtarsal joint of said foot; and
capturing an image of at least one subject area of said foot and/or associated ankle and lower leg so as to determine contours of said subject area with said midtarsal joint of said foot locked.

18. The method of claim 17, wherein the step of capturing an image of said at least one subject area comprises:
capturing an image of said at least one subject area by directing a digital imaging device over a bottom and top of said foot and over said associated ankle and lower leg of said patient.

19. The method of claim 17, wherein the step of providing at least one metatarsal head support member comprises:
providing at least one metatarsal head support member that engages said plantar surface of said foot substantially only beneath an area of fourth and fifth metatarsal heads of said foot.

20. The method of claim 17, wherein the step of providing said at least one metatarsal head support member comprises:
providing a metatarsal head support member that engages said plantar surface of said foot substantially only beneath said fifth metatarsal head of said foot.

21. The method of claim 17, wherein said step of providing said at least one metatarsal head support member comprises:
providing a support and alignment assembly that orientates said foot for imaging and that has said at least one metatarsal head support member mounted thereon.

22. The method of claim 21, wherein the step of providing a support and alignment assembly comprises:
providing a support and alignment assembly having a frame that is collapsible from an erected configuration for use to a collapsed configuration for transportation or storage.

23. The method of claim 21, wherein the step of moving said lateral forefoot area of said foot relative to said at least one metatarsal head support member so that said lateral forefoot area of said foot is reactively loaded in a dorsal direction by said at least one metatarsal head support member comprises:
engaging said foot with a foot engagement member of said support and alignment assembly; and
translating said foot engagement member towards said at least one metatarsal head support member so that said lateral forefoot area of said foot moves into contact with said at least one metatarsal head support member and is reactively loaded in a dorsal direction thereby.

24. The method of claim 21, wherein the step of moving said lateral forefoot area of said foot relative to said at least one metatarsal head support member so that said lateral forefoot area of said foot is reactively loaded in a dorsal direction by said at least one metatarsal head support member comprises:

maintaining said foot in alignment with said support and alignment assembly; and translating said support and alignment assembly towards said foot so that said at least one metatarsal head support member moves into contact with said lateral forefoot area of said foot and said lateral forefoot area is reactively loaded in a dorsal direction thereby.

25. The method of claim 21, wherein the step of moving the lateral forefoot area of the foot relative to said at least one metatarsal head support member so that said lateral forefoot area of said foot is reactively loaded in a dorsal direction comprises:

positioning a plantar surface of a heel of said foot against a heel support member substantially in a common plane with said metatarsal head support member; and plantarflexing said foot against said metatarsal head support member to reactively load said lateral forefoot area of said foot in said dorsal direction.

26. The method of claim 17, further comprising the step of:

constructing an orthotic device from said contours determined from said image captured of at least one subject area of said foot and/or associated ankle and lower leg.

27. The method of claim 26, wherein the step of constructing an orthotic device comprises:

constructing an orthotic shoe insert from contours determined from images captured of a plantar surface of said foot.

28. The method of claim 26, wherein the step of constructing an orthotic device comprises:

constructing an ankle foot orthotic from contours determined from images captured of an upper portion of said foot and from surfaces of said associated ankle and lower leg.

29. The method of claim 17, further comprising the step of:

determining a volume of said subject area of said foot and/or associated ankle and lower leg from said contours determined from images captured of said at least one subject area.

30. The method of claim 29, further comprising the step of:

constructing an orthotic device that cooperates with said subject area of said foot and/or associated ankle and lower leg for which said volume has been determined.

31. The method of claim 30, wherein the step of constructing an orthotic device that cooperates with said subject area of said foot and/or associated ankle and lower leg comprises:

comparing said determined volume of said subject area of said foot and/or associated ankle and lower leg with an interior volume of an article that receives said foot and/or associated ankle and lower leg so as to determine a remaining volume within said article; and constructing said orthotic device to have a volume that corresponds to said remaining volume within said article so that in combination with said orthotic device the subject area of said foot and/or associated ankle and lower leg is received in said article with a desired degree of fit.

32. The method of claim 30, wherein the step of constructing an orthotic device that cooperates with said subject area of said foot and/or associated ankle and lower leg comprises:

constructing an orthotic device that surrounds said subject area of said foot and/or associated ankle and lower leg to have a volume that corresponds to said determined volume of said subject area.

33. The method of claim 32, wherein the step of constructing said orthotic device that surrounds said subject area of said foot and/or associated ankle and lower leg comprises:

constructing an ankle-foot orthotic that engages an upper portion of said foot and surrounds sides of said associated ankle.

* * * * *